United States Patent
Biebl et al.

(10) Patent No.: US 11,427,812 B2
(45) Date of Patent: Aug. 30, 2022

(54) ANTIMICROBIAL AGENTS AGAINST STAPHYLOCOCCUS AUREUS

(71) Applicant: LYSANDO AG, Triesenberg (LI)

(72) Inventors: Manfred Biebl, Obertraubling (DE); Martin Griessl, Hohenschambach (DE); Kristin Neumann, Bamberg (DE)

(73) Assignee: LYSANDO AG, Triesenberg (LI)

( * ) Notice: Subject to any disclaimer, the term of this patent is extended or adjusted under 35 U.S.C. 154(b) by 190 days.

(21) Appl. No.: 16/461,816

(22) PCT Filed: Nov. 20, 2017

(86) PCT No.: PCT/EP2017/079769
§ 371 (c)(1),
(2) Date: May 17, 2019

(87) PCT Pub. No.: WO2018/091707
PCT Pub. Date: May 24, 2018

(65) Prior Publication Data
US 2019/0359962 A1    Nov. 28, 2019

(30) Foreign Application Priority Data

Nov. 18, 2016 (EP) .................... 16199528

(51) Int. Cl.
| | |
|---|---|
| *C12N 9/24* | (2006.01) |
| *A61P 31/04* | (2006.01) |
| *A61L 2/16* | (2006.01) |
| *C12N 9/10* | (2006.01) |
| *C12N 9/52* | (2006.01) |
| *C12N 9/62* | (2006.01) |
| *A61K 38/08* | (2019.01) |
| *A61K 38/00* | (2006.01) |
| *C12N 9/36* | (2006.01) |
| *C12N 9/64* | (2006.01) |

(52) U.S. Cl.
CPC ............ *C12N 9/2462* (2013.01); *A61K 38/08* (2013.01); *A61L 2/16* (2013.01); *A61P 31/04* (2018.01); *C12N 9/1025* (2013.01); *C12N 9/52* (2013.01); *C12N 9/6424* (2013.01); *C12Y 302/01017* (2013.01); *C12Y 304/24075* (2013.01); *A61K 38/00* (2013.01); *A61L 2202/25* (2013.01)

(58) Field of Classification Search
None
See application file for complete search history.

(56) References Cited

U.S. PATENT DOCUMENTS

2016/0097044 A1    4/2016  Donovan

FOREIGN PATENT DOCUMENTS

| EP | 2338916 | 6/2011 |
| EP | 2468856 | 6/2012 |
| JP | 2010-512761 | 4/2010 |
| WO | WO 2008/077397 | 7/2008 |
| WO | WO 2015/121443 | 8/2015 |
| WO | WO 2016/142445 | 9/2016 |
| WO | WO 2018/091707 | 5/2018 |

OTHER PUBLICATIONS

Becker et al., "Triple-acting Lytic Enzyme Treatment of Drug-Resistant and Intracellular *Staphylococcus aureus*", Scientific Reports, vol. 6, No. 1, pp. 1-10. DOI: 10.1038/srep25063.*
Sabala et al., "Crystal structure of the antimicrobial peptidase lysostaphin from *Staphylococcus simulans*", The FEBS Journal, 2014, vol. 281, pp. 4112-4122. doi:10.1111/febs.12929.*
Lu et al., "Cell Wall-targeting Domain of Glycylglycine Endopeptidase Distinguishes among Peptidoglycan Cross-bridges", JBC, 2006, vol. 281, No. 1, pp. 549-558.*
Sans-Gaitero et al., "Crystal structure of the lytic CHAPK domain of the endolysin LysKfrom *Staphylococcus aureus* bacteriophage K", Virology J., 2014, vol. 11, pp. 1-10.*
Becker, Stephen C., et al. "Triple-acting lytic enzyme treatment of drug-resistant and intracellular *Staphylococcus aureus*." *Scientific Reports* 6.1 (2016): 1-10.
Briers, Yves, and Rob Lavigne. "Breaking barriers: expansion of the use of endolysins as novel antibacterials against Gram-negative bacteria." *Future microbiology* 10.3 (2015): 377-390.
Briers, Yves, et al. "A standardized approach for accurate quantification of murein hydrolase activity in high-throughput assays." *Journal of biochemical and biophysical methods* 70.3 (2007): 531-533.
Ding, J. L., P. Li, and B. Ho. "The Sushi peptides: structural characterization and mode of action against Gram-negative bacteria." *Cellular and Molecular Life Sciences* 65.7 (2008): 1202-1219.
International Search Report and Written Opinion issued in International Application No. PCT/EP2017/079769, dated Jun. 8, 2018.
Mitkowski, Pawel, et al. "Structural bases of peptidoglycan recognition by lysostaphin SH3b domain." *Scientific reports* 9.1 (2019): 1-14.

(Continued)

*Primary Examiner* — Suzanne M Noakes
(74) *Attorney, Agent, or Firm* — Parker Highlander PLLC

(57) ABSTRACT

The present invention relates to the field of antimicrobial agents active against *Staphylococcus aureus* bacteria. In particular, the present invention relates to polypeptides comprising the CHAP domain of LysK endolysin, the M23 endopeptidase domain of lysostaphin, the cell wall binding domain (CBD) of ALE-1, and a further peptide selected from the group consisting of an antimicrobial peptide, an amphipathic peptide, a cationic peptide, a hydrophobic peptide, a sushi peptide and a defensin. In addition, the present invention relates to nucleic acids encoding such polypeptides, vectors comprising such nucleic acids, and corresponding host cells, compositions and devices. Finally, the present invention relates to applications of the inventive polypeptides, in particular in the pharmaceutical field.

37 Claims, No Drawings
Specification includes a Sequence Listing.

(56) References Cited

OTHER PUBLICATIONS

Tan, Nguan Soon, et al. "Definition of endotoxin binding sites in horseshoe crab factor C recombinant sushi proteins and neutralization of endotoxin by sushi peptides." *The FASEB Journal* 14.12 (2000): 1801-1813.
Office Communication issued in Japanese Application No. 2018-564275, dated Sep. 14, 2021. Original with Machine Translation.

* cited by examiner

SEQUENCE LISTING

```
<160> NUMBER OF SEQ ID NOS: 111

<210> SEQ ID NO 1
<211> LENGTH: 93
<212> TYPE: PRT
<213> ORGANISM: Unknown
<220> FEATURE:
<223> OTHER INFORMATION: CHAP domain of  LysK endolysin

<400> SEQUENCE: 1

Ile Asp Ala Asp Gly Tyr Tyr His Ala Gln Cys Gln Asp Leu Ile Thr
1               5                   10                  15

Asp Tyr Val Leu Trp Leu Thr Asp Asn Lys Val Arg Thr Trp Gly Asn
```

```
                20                  25                  30
Ala Lys Asp Gln Ile Lys Gln Ser Tyr Gly Thr Gly Phe Lys Ile His
            35                  40                  45

Glu Asn Lys Pro Ser Thr Val Pro Lys Lys Gly Trp Ile Ala Val Phe
        50                  55                  60

Thr Ser Gly Ser Tyr Glu Gln Trp Gly His Ile Gly Ile Val Tyr Asp
65                  70                  75                  80

Gly Gly Asn Thr Ser Thr Phe Thr Ile Leu Glu Gln Asn
                85                  90

<210> SEQ ID NO 2
<211> LENGTH: 177
<212> TYPE: PRT
<213> ORGANISM: unknown
<220> FEATURE:
<223> OTHER INFORMATION: N-terminus of LysK endolysin including CHAP
      domain; w/o N-terminal methionine

<400> SEQUENCE: 2

Ala Lys Thr Gln Ala Glu Ile Asn Lys Arg Leu Asp Ala Tyr Ala Lys
1               5                   10                  15

Gly Thr Val Asp Ser Pro Tyr Arg Val Lys Lys Ala Thr Ser Tyr Asp
            20                  25                  30

Pro Ser Phe Gly Val Met Glu Ala Gly Ala Ile Asp Ala Asp Gly Tyr
        35                  40                  45

Tyr His Ala Gln Cys Gln Asp Leu Ile Thr Asp Tyr Val Leu Trp Leu
    50                  55                  60

Thr Asp Asn Lys Val Arg Thr Trp Gly Asn Ala Lys Asp Gln Ile Lys
65                  70                  75                  80

Gln Ser Tyr Gly Thr Gly Phe Lys Ile His Glu Asn Lys Pro Ser Thr
                85                  90                  95

Val Pro Lys Lys Gly Trp Ile Ala Val Phe Thr Ser Gly Ser Tyr Glu
            100                 105                 110

Gln Trp Gly His Ile Gly Ile Val Tyr Asp Gly Gly Asn Thr Ser Thr
        115                 120                 125

Phe Thr Ile Leu Glu Gln Asn Trp Asn Gly Tyr Ala Asn Lys Lys Pro
    130                 135                 140

Thr Lys Arg Val Asp Asn Tyr Tyr Gly Leu Thr His Phe Ile Glu Ile
145                 150                 155                 160

Pro Val Lys Ala Gly Thr Thr Val Lys Lys Glu Thr Ala Lys Lys Ser
                165                 170                 175

Ala

<210> SEQ ID NO 3
<211> LENGTH: 102
<212> TYPE: PRT
<213> ORGANISM: Staphylococcus simulans

<400> SEQUENCE: 3

Gly Met His Tyr Gly Val Asp Phe Phe Met Asn Ile Gly Thr Pro Val
1               5                   10                  15

Lys Ala Ile Ser Ser Gly Lys Ile Val Glu Ala Gly Trp Ser Asn Tyr
            20                  25                  30

Gly Gly Gly Asn Gln Ile Gly Leu Ile Glu Asn Asp Gly Val His Arg
        35                  40                  45

Gln Trp Tyr Met His Leu Ser Lys Tyr Asn Val Lys Val Gly Asp Tyr
    50                  55                  60
```

Val Lys Ala Gly Gln Ile Ile Gly Trp Ser Gly Ser Thr Gly Tyr Ser
65                  70                  75                  80

Thr Ala Pro His Leu His Phe Gln Arg Met Val Asn Ser Phe Ser Asn
                85                  90                  95

Ser Thr Ala Gln Asp Pro
            100

<210> SEQ ID NO 4
<211> LENGTH: 149
<212> TYPE: PRT
<213> ORGANISM: Staphylococcus simulans

<400> SEQUENCE: 4

His Glu His Ser Ala Gln Trp Leu Asn Asn Tyr Lys Lys Gly Tyr Gly
1               5                   10                  15

Tyr Gly Pro Tyr Pro Leu Gly Ile Asn Gly Gly Met His Tyr Gly Val
            20                  25                  30

Asp Phe Phe Met Asn Ile Gly Thr Pro Val Lys Ala Ile Ser Ser Gly
        35                  40                  45

Lys Ile Val Glu Ala Gly Trp Ser Asn Tyr Gly Gly Gly Asn Gln Ile
50                  55                  60

Gly Leu Ile Glu Asn Asp Gly Val His Arg Gln Trp Tyr Met His Leu
65                  70                  75                  80

Ser Lys Tyr Asn Val Lys Val Gly Asp Tyr Val Lys Ala Gly Gln Ile
                85                  90                  95

Ile Gly Trp Ser Gly Ser Thr Gly Tyr Ser Thr Ala Pro His Leu His
            100                 105                 110

Phe Gln Arg Met Val Asn Ser Phe Ser Asn Ser Thr Ala Gln Asp Pro
        115                 120                 125

Met Pro Phe Leu Lys Ser Ala Gly Tyr Gly Lys Ala Gly Gly Thr Val
    130                 135                 140

Thr Pro Thr Pro Asn
145

<210> SEQ ID NO 5
<211> LENGTH: 69
<212> TYPE: PRT
<213> ORGANISM: Staphylococcus capitis EPK1

<400> SEQUENCE: 5

Ser Glu Ser Ala Ser Phe Thr Ala Asn Thr Asp Ile Ile Thr Arg Leu
1               5                   10                  15

Thr Gly Pro Phe Arg Ser Met Pro Gln Ser Gly Val Leu Arg Lys Gly
            20                  25                  30

Leu Thr Ile Lys Tyr Asp Glu Val Met Lys Gln Asp Gly His Val Trp
        35                  40                  45

Val Gly Tyr Asn Thr Asn Ser Gly Lys Arg Val Tyr Leu Pro Val Arg
    50                  55                  60

Thr Trp Asn Glu Ser
65

<210> SEQ ID NO 6
<211> LENGTH: 94
<212> TYPE: PRT
<213> ORGANISM: Staphylococcus capitis EPK1

<400> SEQUENCE: 6

```
Asn Gly Tyr Lys Thr Asn Lys Tyr Gly Thr Leu Tyr Lys Ser Glu Ser
1               5                   10                  15

Ala Ser Phe Thr Ala Asn Thr Asp Ile Ile Thr Arg Leu Thr Gly Pro
            20                  25                  30

Phe Arg Ser Met Pro Gln Ser Gly Val Leu Arg Lys Gly Leu Thr Ile
        35                  40                  45

Lys Tyr Asp Glu Val Met Lys Gln Asp Gly His Val Trp Val Gly Tyr
    50                  55                  60

Asn Thr Asn Ser Gly Lys Arg Val Tyr Leu Pro Val Arg Thr Trp Asn
65                  70                  75                  80

Glu Ser Thr Gly Glu Leu Gly Pro Leu Trp Gly Thr Ile Lys
                85                  90
```

<210> SEQ ID NO 7
<211> LENGTH: 5
<212> TYPE: PRT
<213> ORGANISM: Artificial
<220> FEATURE:
<223> OTHER INFORMATION: Linker sequence

<400> SEQUENCE: 7

```
Gly Gly Gly Gly Ser
1               5
```

<210> SEQ ID NO 8
<211> LENGTH: 245
<212> TYPE: PRT
<213> ORGANISM: Artificial sequence
<220> FEATURE:
<223> OTHER INFORMATION: Sequence comprising M23 endopeptidase domain of
      lysostaphin and the cell wall binding domain of ALE-1 endolysin

<400> SEQUENCE: 8

```
His Glu His Ser Ala Gln Trp Leu Asn Asn Tyr Lys Lys Gly Tyr Gly
1               5                   10                  15

Tyr Gly Pro Tyr Pro Leu Gly Ile Asn Gly Gly Met His Tyr Gly Val
            20                  25                  30

Asp Phe Phe Met Asn Ile Gly Thr Pro Val Lys Ala Ile Ser Ser Gly
        35                  40                  45

Lys Ile Val Glu Ala Gly Trp Ser Asn Tyr Gly Gly Gly Asn Gln Ile
    50                  55                  60

Gly Leu Ile Glu Asn Asp Gly Val His Arg Gln Trp Tyr Met His Leu
65                  70                  75                  80

Ser Lys Tyr Asn Val Lys Val Gly Asp Tyr Val Lys Ala Gly Gln Ile
                85                  90                  95

Ile Gly Trp Ser Gly Ser Thr Gly Tyr Ser Thr Ala Pro His Leu His
            100                 105                 110

Phe Gln Arg Met Val Asn Ser Phe Ser Asn Ser Thr Ala Gln Asp Pro
        115                 120                 125

Met Pro Phe Leu Lys Ser Ala Gly Tyr Gly Lys Ala Gly Gly Thr Val
    130                 135                 140

Thr Pro Thr Pro Asn Pro Gly Asn Gly Tyr Lys Thr Asn Lys Tyr Gly
145                 150                 155                 160

Thr Leu Tyr Lys Ser Glu Ser Ala Ser Phe Thr Ala Asn Thr Asp Ile
                165                 170                 175

Ile Thr Arg Leu Thr Gly Pro Phe Arg Ser Met Pro Gln Ser Gly Val
            180                 185                 190

Leu Arg Lys Gly Leu Thr Ile Lys Tyr Asp Glu Val Met Lys Gln Asp
```

```
                195                 200                 205
Gly His Val Trp Val Gly Tyr Asn Thr Asn Ser Gly Lys Arg Val Tyr
    210                 215                 220

Leu Pro Val Arg Thr Trp Asn Glu Ser Thr Gly Glu Leu Gly Pro Leu
225                 230                 235                 240

Trp Gly Thr Ile Lys
            245

<210> SEQ ID NO 9
<211> LENGTH: 424
<212> TYPE: PRT
<213> ORGANISM: artificial sequence
<220> FEATURE:
<223> OTHER INFORMATION: Fusion protein comprising CHAP domain of LysK
      endolysin, M23 endopeptidase domain of lysostaphin and the cell
      wall binding domain of ALE-1 endolysin; w/o N-terminal Methionine

<400> SEQUENCE: 9

Ala Lys Thr Gln Ala Glu Ile Asn Lys Arg Leu Asp Ala Tyr Ala Lys
1               5                   10                  15

Gly Thr Val Asp Ser Pro Tyr Arg Val Lys Lys Ala Thr Ser Tyr Asp
            20                  25                  30

Pro Ser Phe Gly Val Met Glu Ala Gly Ala Ile Asp Ala Asp Gly Tyr
        35                  40                  45

Tyr His Ala Gln Cys Gln Asp Leu Ile Thr Asp Tyr Val Leu Trp Leu
    50                  55                  60

Thr Asp Asn Lys Val Arg Thr Trp Gly Asn Ala Lys Asp Gln Ile Lys
65                  70                  75                  80

Gln Ser Tyr Gly Thr Gly Phe Lys Ile His Glu Asn Lys Pro Ser Thr
                85                  90                  95

Val Pro Lys Lys Gly Trp Ile Ala Val Phe Thr Ser Gly Ser Tyr Glu
            100                 105                 110

Gln Trp Gly His Ile Gly Ile Val Tyr Asp Gly Gly Asn Thr Ser Thr
        115                 120                 125

Phe Thr Ile Leu Glu Gln Asn Trp Asn Gly Tyr Ala Asn Lys Lys Pro
    130                 135                 140

Thr Lys Arg Val Asp Asn Tyr Tyr Gly Leu Thr His Phe Ile Glu Ile
145                 150                 155                 160

Pro Val Lys Ala Gly Thr Thr Val Lys Lys Glu Thr Ala Lys Lys Ser
                165                 170                 175

Ala Thr Ser His Glu His Ser Ala Gln Trp Leu Asn Asn Tyr Lys Lys
            180                 185                 190

Gly Tyr Gly Tyr Gly Pro Tyr Pro Leu Gly Ile Asn Gly Gly Met His
        195                 200                 205

Tyr Gly Val Asp Phe Phe Met Asn Ile Gly Thr Pro Val Lys Ala Ile
    210                 215                 220

Ser Ser Gly Lys Ile Val Glu Ala Gly Trp Ser Asn Tyr Gly Gly Gly
225                 230                 235                 240

Asn Gln Ile Gly Leu Ile Glu Asn Asp Gly Val His Arg Gln Trp Tyr
                245                 250                 255

Met His Leu Ser Lys Tyr Asn Val Lys Val Gly Asp Tyr Val Lys Ala
            260                 265                 270

Gly Gln Ile Ile Gly Trp Ser Gly Ser Thr Gly Tyr Ser Thr Ala Pro
        275                 280                 285

His Leu His Phe Gln Arg Met Val Asn Ser Phe Ser Asn Ser Thr Ala
    290                 295                 300
```

```
Gln Asp Pro Met Pro Phe Leu Lys Ser Ala Gly Tyr Gly Lys Ala Gly
305                 310                 315                 320

Gly Thr Val Thr Pro Thr Asn Pro Gly Asn Gly Tyr Lys Thr Asn
                325                 330                 335

Lys Tyr Gly Thr Leu Tyr Lys Ser Glu Ser Ala Ser Phe Thr Ala Asn
            340                 345                 350

Thr Asp Ile Ile Thr Arg Leu Thr Gly Pro Phe Arg Ser Met Pro Gln
            355                 360                 365

Ser Gly Val Leu Arg Lys Gly Leu Thr Ile Lys Tyr Asp Glu Val Met
370                 375                 380

Lys Gln Asp Gly His Val Trp Val Gly Tyr Asn Thr Asn Ser Gly Lys
385                 390                 395                 400

Arg Val Tyr Leu Pro Val Arg Thr Trp Asn Glu Ser Thr Gly Glu Leu
                405                 410                 415

Gly Pro Leu Trp Gly Thr Ile Lys
                420
```

<210> SEQ ID NO 10
<211> LENGTH: 425
<212> TYPE: PRT
<213> ORGANISM: artificial sequence
<220> FEATURE:
<223> OTHER INFORMATION: Fusion protein comprising CHAP domain of LysK
      endolysin, M23 endopeptidase domain of lysostaphin and the cell
      wall binding domain of ALE-1 endolysin

<400> SEQUENCE: 10

```
Met Ala Lys Thr Gln Ala Glu Ile Asn Lys Arg Leu Asp Ala Tyr Ala
1               5                   10                  15

Lys Gly Thr Val Asp Ser Pro Tyr Arg Val Lys Lys Ala Thr Ser Tyr
            20                  25                  30

Asp Pro Ser Phe Gly Val Met Glu Ala Gly Ala Ile Asp Ala Asp Gly
        35                  40                  45

Tyr Tyr His Ala Gln Cys Gln Asp Leu Ile Thr Asp Tyr Val Leu Trp
    50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
            100                 105                 110

Glu Gln Trp Gly His Ile Gly Ile Val Tyr Asp Gly Asn Thr Ser
        115                 120                 125

Thr Phe Thr Ile Leu Glu Gln Asn Trp Asn Gly Tyr Ala Asn Lys Lys
    130                 135                 140

Pro Thr Lys Arg Val Asp Asn Tyr Tyr Gly Leu Thr His Phe Ile Glu
145                 150                 155                 160

Ile Pro Val Lys Ala Gly Thr Thr Val Lys Lys Glu Thr Ala Lys Lys
                165                 170                 175

Ser Ala Thr Ser His Glu His Ser Ala Gln Trp Leu Asn Asn Tyr Lys
            180                 185                 190

Lys Gly Tyr Gly Tyr Gly Pro Tyr Pro Leu Gly Ile Asn Gly Gly Met
        195                 200                 205

His Tyr Gly Val Asp Phe Phe Met Asn Ile Gly Thr Pro Val Lys Ala
    210                 215                 220
```

Ile Ser Ser Gly Lys Ile Val Glu Ala Gly Trp Ser Asn Tyr Gly Gly
225                 230                 235                 240

Gly Asn Gln Ile Gly Leu Ile Glu Asn Asp Gly Val His Arg Gln Trp
            245                 250                 255

Tyr Met His Leu Ser Lys Tyr Asn Val Lys Val Gly Asp Tyr Val Lys
        260                 265                 270

Ala Gly Gln Ile Ile Gly Trp Ser Gly Ser Thr Gly Tyr Ser Thr Ala
    275                 280                 285

Pro His Leu His Phe Gln Arg Met Val Asn Ser Phe Ser Asn Ser Thr
    290                 295                 300

Ala Gln Asp Pro Met Pro Phe Leu Lys Ser Ala Gly Tyr Gly Lys Ala
305                 310                 315                 320

Gly Gly Thr Val Thr Pro Thr Pro Asn Pro Gly Asn Gly Tyr Lys Thr
            325                 330                 335

Asn Lys Tyr Gly Thr Leu Tyr Lys Ser Glu Ser Ala Ser Phe Thr Ala
        340                 345                 350

Asn Thr Asp Ile Ile Thr Arg Leu Thr Gly Pro Phe Arg Ser Met Pro
    355                 360                 365

Gln Ser Gly Val Leu Arg Lys Gly Leu Thr Ile Lys Tyr Asp Glu Val
    370                 375                 380

Met Lys Gln Asp Gly His Val Trp Val Gly Tyr Asn Thr Asn Ser Gly
385                 390                 395                 400

Lys Arg Val Tyr Leu Pro Val Arg Thr Trp Asn Glu Ser Thr Gly Glu
            405                 410                 415

Leu Gly Pro Leu Trp Gly Thr Ile Lys
            420                 425

<210> SEQ ID NO 11
<211> LENGTH: 6
<212> TYPE: PRT
<213> ORGANISM: artificial
<220> FEATURE:
<223> OTHER INFORMATION: synthetic sequence

<400> SEQUENCE: 11

Lys Arg Lys Lys Arg Lys
1               5

<210> SEQ ID NO 12
<211> LENGTH: 5
<212> TYPE: PRT
<213> ORGANISM: artificial
<220> FEATURE:
<223> OTHER INFORMATION: synethtic sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 12

Lys Arg Xaa Lys Arg
1               5

<210> SEQ ID NO 13
<211> LENGTH: 5
<212> TYPE: PRT
<213> ORGANISM: artificial
<220> FEATURE:
<223> OTHER INFORMATION: synthetic sequence

<400> SEQUENCE: 13

Lys Arg Ser Lys Arg
1               5

<210> SEQ ID NO 14
<211> LENGTH: 5
<212> TYPE: PRT
<213> ORGANISM: artificial
<220> FEATURE:
<223> OTHER INFORMATION: synthetic sequence

<400> SEQUENCE: 14

Lys Arg Gly Ser Gly
1               5

<210> SEQ ID NO 15
<211> LENGTH: 9
<212> TYPE: PRT
<213> ORGANISM: artificial
<220> FEATURE:
<223> OTHER INFORMATION: synthetic sequence

<400> SEQUENCE: 15

Lys Arg Lys Lys Arg Lys Lys Arg Lys
1               5

<210> SEQ ID NO 16
<211> LENGTH: 9
<212> TYPE: PRT
<213> ORGANISM: artificial
<220> FEATURE:
<223> OTHER INFORMATION: synthetic sequence

<400> SEQUENCE: 16

Arg Arg Arg Arg Arg Arg Arg Arg Arg
1               5

<210> SEQ ID NO 17
<211> LENGTH: 8
<212> TYPE: PRT
<213> ORGANISM: artificial
<220> FEATURE:
<223> OTHER INFORMATION: synthetic sequence

<400> SEQUENCE: 17

Lys Lys Lys Lys Lys Lys Lys Lys
1               5

<210> SEQ ID NO 18
<211> LENGTH: 10
<212> TYPE: PRT
<213> ORGANISM: artificial
<220> FEATURE:
<223> OTHER INFORMATION: synthetic sequence

<400> SEQUENCE: 18

Lys Arg Lys Lys Arg Lys Lys Arg Lys Lys
1               5                   10

<210> SEQ ID NO 19
<211> LENGTH: 12
<212> TYPE: PRT
<213> ORGANISM: artificial
<220> FEATURE:
<223> OTHER INFORMATION: synthetic sequence

<400> SEQUENCE: 19

Lys Arg Lys Lys Arg Lys Lys Arg Lys Lys Arg Lys

```
1               5                  10

<210> SEQ ID NO 20
<211> LENGTH: 14
<212> TYPE: PRT
<213> ORGANISM: artificial
<220> FEATURE:
<223> OTHER INFORMATION: synthetic sequence

<400> SEQUENCE: 20

Lys Arg Lys Lys Arg Lys Lys Arg Lys Lys Arg Lys Lys Arg
1               5                  10

<210> SEQ ID NO 21
<211> LENGTH: 16
<212> TYPE: PRT
<213> ORGANISM: artificial
<220> FEATURE:
<223> OTHER INFORMATION: synthetic sequence

<400> SEQUENCE: 21

Lys Lys Lys Lys Lys Lys Lys Lys Lys Lys Lys Lys Lys Lys Lys Lys
1               5                  10                  15

<210> SEQ ID NO 22
<211> LENGTH: 18
<212> TYPE: PRT
<213> ORGANISM: artificial
<220> FEATURE:
<223> OTHER INFORMATION: synthetic sequence

<400> SEQUENCE: 22

Lys Arg Lys Lys Arg Lys Lys Arg Lys Lys Arg Lys Lys Arg Lys Lys
1               5                  10                  15

Arg Lys

<210> SEQ ID NO 23
<211> LENGTH: 19
<212> TYPE: PRT
<213> ORGANISM: artificial
<220> FEATURE:
<223> OTHER INFORMATION: synthetic sequence

<400> SEQUENCE: 23

Lys Arg Lys Lys Arg Lys Lys Arg Lys Lys Arg Lys Lys Arg Lys Lys
1               5                  10                  15

Arg Lys Lys

<210> SEQ ID NO 24
<211> LENGTH: 19
<212> TYPE: PRT
<213> ORGANISM: artificial
<220> FEATURE:
<223> OTHER INFORMATION: synthetic sequence

<400> SEQUENCE: 24

Arg Arg Arg Arg Arg Arg Arg Arg Arg Arg Arg Arg Arg Arg Arg Arg
1               5                  10                  15

Arg Arg Arg

<210> SEQ ID NO 25
<211> LENGTH: 19
<212> TYPE: PRT
<213> ORGANISM: artificial
<220> FEATURE:
```

<223> OTHER INFORMATION: synthetic sequence

<400> SEQUENCE: 25

Lys Lys Lys Lys Lys Lys Lys Lys Lys Lys Lys Lys Lys Lys Lys
1               5                   10                  15

Lys Lys Lys

<210> SEQ ID NO 26
<211> LENGTH: 20
<212> TYPE: PRT
<213> ORGANISM: artificial
<220> FEATURE:
<223> OTHER INFORMATION: synthetic sequence

<400> SEQUENCE: 26

Lys Arg Lys Lys Arg Lys Lys Arg Lys Arg Ser Lys Arg Lys Lys Arg
1               5                   10                  15

Lys Lys Arg Lys
            20

<210> SEQ ID NO 27
<211> LENGTH: 21
<212> TYPE: PRT
<213> ORGANISM: artificial
<220> FEATURE:
<223> OTHER INFORMATION: synthetic sequence

<400> SEQUENCE: 27

Lys Arg Lys Lys Arg Lys Lys Arg Lys Arg Ser Lys Arg Lys Lys Arg
1               5                   10                  15

Lys Lys Arg Lys Lys
            20

<210> SEQ ID NO 28
<211> LENGTH: 21
<212> TYPE: PRT
<213> ORGANISM: artificial
<220> FEATURE:
<223> OTHER INFORMATION: synthetic sequence

<400> SEQUENCE: 28

Lys Arg Lys Lys Arg Lys Lys Arg Lys Lys Arg Lys Lys Arg Lys Lys
1               5                   10                  15

Arg Lys Lys Arg Lys
            20

<210> SEQ ID NO 29
<211> LENGTH: 22
<212> TYPE: PRT
<213> ORGANISM: artificial
<220> FEATURE:
<223> OTHER INFORMATION: synthetic sequence

<400> SEQUENCE: 29

Lys Arg Lys Lys Arg Lys Lys Arg Lys Arg Gly Ser Gly Lys Arg Lys
1               5                   10                  15

Lys Arg Lys Lys Arg Lys
            20

<210> SEQ ID NO 30
<211> LENGTH: 24
<212> TYPE: PRT
<213> ORGANISM: artificial
<220> FEATURE:

<223> OTHER INFORMATION: synthetic sequence

<400> SEQUENCE: 30

Lys Arg Lys Lys Arg Lys Lys Arg Lys Arg Gly Ser Gly Ser Gly Lys
1               5                   10                  15

Arg Lys Lys Arg Lys Lys Arg Lys
            20

<210> SEQ ID NO 31
<211> LENGTH: 25
<212> TYPE: PRT
<213> ORGANISM: artificial
<220> FEATURE:
<223> OTHER INFORMATION: synthetic sequence

<400> SEQUENCE: 31

Lys Arg Lys Lys Arg Lys Lys Arg Lys Arg Lys Lys Arg Lys Lys
1               5                   10                  15

Arg Lys Lys Arg Lys Lys Arg Lys Lys
            20                  25

<210> SEQ ID NO 32
<211> LENGTH: 31
<212> TYPE: PRT
<213> ORGANISM: artificial
<220> FEATURE:
<223> OTHER INFORMATION: synthetic sequence

<400> SEQUENCE: 32

Lys Arg Lys Lys Arg Lys Lys Arg Lys Arg Ser Lys Arg Lys Lys Arg
1               5                   10                  15

Lys Lys Arg Lys Arg Ser Lys Arg Lys Lys Arg Lys Lys Arg Lys
            20                  25                  30

<210> SEQ ID NO 33
<211> LENGTH: 38
<212> TYPE: PRT
<213> ORGANISM: artificial
<220> FEATURE:
<223> OTHER INFORMATION: synthetic sequence

<400> SEQUENCE: 33

Lys Arg Lys Lys Arg Lys Lys Arg Lys Arg Gly Ser Gly Ser Gly Lys
1               5                   10                  15

Arg Lys Lys Arg Lys Lys Arg Lys Gly Ser Gly Ser Gly Lys Arg Lys
            20                  25                  30

Lys Arg Lys Lys Arg Lys
        35

<210> SEQ ID NO 34
<211> LENGTH: 39
<212> TYPE: PRT
<213> ORGANISM: artificial
<220> FEATURE:
<223> OTHER INFORMATION: synthetic sequence

<400> SEQUENCE: 34

Lys Arg Lys Lys Arg Lys Lys Arg Lys Lys Arg Lys Lys Arg Lys Lys
1               5                   10                  15

Arg Lys Lys Arg Lys Lys Arg Lys Lys Arg Lys Lys Arg Lys Lys Arg
            20                  25                  30

Lys Lys Arg Lys Lys Arg Lys
        35

```
<210> SEQ ID NO 35
<211> LENGTH: 42
<212> TYPE: PRT
<213> ORGANISM: artificial
<220> FEATURE:
<223> OTHER INFORMATION: synthetic sequence

<400> SEQUENCE: 35

Lys Arg Lys Lys Arg Lys Lys Arg Lys Arg Ser Lys Arg Lys Lys Arg
1               5                   10                  15

Lys Lys Arg Lys Arg Ser Lys Arg Lys Lys Arg Lys Lys Arg Lys Arg
            20                  25                  30

Ser Lys Arg Lys Lys Arg Lys Lys Arg Lys
            35                  40

<210> SEQ ID NO 36
<211> LENGTH: 3
<212> TYPE: PRT
<213> ORGANISM: Artificial sequence
<220> FEATURE:
<223> OTHER INFORMATION: cationic peptide KNA

<400> SEQUENCE: 36

Lys Asn Ala
1

<210> SEQ ID NO 37
<211> LENGTH: 6
<212> TYPE: PRT
<213> ORGANISM: Artificial sequence
<220> FEATURE:
<223> OTHER INFORMATION: cationic peptide GGSKNA

<400> SEQUENCE: 37

Gly Gly Ser Lys Asn Ala
1               5

<210> SEQ ID NO 38
<211> LENGTH: 3
<212> TYPE: PRT
<213> ORGANISM: Artificial sequence
<220> FEATURE:
<223> OTHER INFORMATION: cationic peptide KNK

<400> SEQUENCE: 38

Lys Asn Lys
1

<210> SEQ ID NO 39
<211> LENGTH: 6
<212> TYPE: PRT
<213> ORGANISM: Artificial sequence
<220> FEATURE:
<223> OTHER INFORMATION: cationic peptide GGSKNK

<400> SEQUENCE: 39

Gly Gly Ser Lys Asn Lys
1               5

<210> SEQ ID NO 40
<211> LENGTH: 37
<212> TYPE: PRT
<213> ORGANISM: Homo sapiens

<400> SEQUENCE: 40
```

```
Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
                20                  25                  30

Pro Arg Thr Glu Ser
            35

<210> SEQ ID NO 41
<211> LENGTH: 29
<212> TYPE: PRT
<213> ORGANISM: unknown
<220> FEATURE:
<223> OTHER INFORMATION: SMAP-29 sheep

<400> SEQUENCE: 41

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly
                20                  25

<210> SEQ ID NO 42
<211> LENGTH: 13
<212> TYPE: PRT
<213> ORGANISM: unknown
<220> FEATURE:
<223> OTHER INFORMATION: Indolicidine bovine

<400> SEQUENCE: 42

Ile Leu Pro Trp Lys Trp Pro Trp Trp Pro Trp Arg Arg
1               5                   10

<210> SEQ ID NO 43
<211> LENGTH: 18
<212> TYPE: PRT
<213> ORGANISM: unknown
<220> FEATURE:
<223> OTHER INFORMATION: Protegrin Porcine

<400> SEQUENCE: 43

Arg Gly Gly Arg Leu Cys Tyr Cys Arg Arg Arg Phe Cys Val Cys Val
1               5                   10                  15

Gly Arg

<210> SEQ ID NO 44
<211> LENGTH: 31
<212> TYPE: PRT
<213> ORGANISM: unknown
<220> FEATURE:
<223> OTHER INFORMATION: Cecropin P1 Mammal (pig)

<400> SEQUENCE: 44

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
                20                  25                  30

<210> SEQ ID NO 45
<211> LENGTH: 23
<212> TYPE: PRT
<213> ORGANISM: unknown
<220> FEATURE:
<223> OTHER INFORMATION: Magainin frog

<400> SEQUENCE: 45
```

```
Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 46
<211> LENGTH: 25
<212> TYPE: PRT
<213> ORGANISM: unknown
<220> FEATURE:
<223> OTHER INFORMATION: Pleurocidin fish

<400> SEQUENCE: 46

Gly Trp Gly Ser Phe Phe Lys Lys Ala Ala His Val Gly Lys His Val
1               5                   10                  15

Gly Lys Ala Ala Leu Thr His Tyr Leu
            20                  25

<210> SEQ ID NO 47
<211> LENGTH: 36
<212> TYPE: PRT
<213> ORGANISM: Aedes aegypti

<400> SEQUENCE: 47

Gly Gly Leu Lys Lys Leu Gly Lys Lys Leu Glu Gly Ala Gly Lys Arg
1               5                   10                  15

Val Phe Asn Ala Ala Glu Lys Ala Leu Pro Val Val Ala Gly Ala Lys
            20                  25                  30

Ala Leu Arg Lys
            35

<210> SEQ ID NO 48
<211> LENGTH: 40
<212> TYPE: PRT
<213> ORGANISM: Drosophila melanogaster

<400> SEQUENCE: 48

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Pro Gln Gln Ala Ala
            20                  25                  30

Asn Val Ala Ala Thr Ala Arg Gly
            35                  40

<210> SEQ ID NO 49
<211> LENGTH: 21
<212> TYPE: PRT
<213> ORGANISM: unknown
<220> FEATURE:
<223> OTHER INFORMATION: Buforin II vertebrate

<400> SEQUENCE: 49

Thr Arg Ser Ser Arg Ala Gly Leu Gln Phe Pro Val Gly Arg Val His
1               5                   10                  15

Arg Leu Leu Arg Lys
            20

<210> SEQ ID NO 50
<211> LENGTH: 39
<212> TYPE: PRT
<213> ORGANISM: unknown
<220> FEATURE:
```

```
<223> OTHER INFORMATION: Sarcotoxin IA Fly

<400> SEQUENCE: 50

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Ala Gln Gln Ala Ala
            20                  25                  30

Asn Val Ala Ala Thr Ala Arg
        35

<210> SEQ ID NO 51
<211> LENGTH: 17
<212> TYPE: PRT
<213> ORGANISM: Apis mellifera

<400> SEQUENCE: 51

Ala Asn Arg Pro Val Tyr Ile Pro Pro Pro Arg Pro Pro His Pro Arg
1               5                   10                  15

Leu

<210> SEQ ID NO 52
<211> LENGTH: 24
<212> TYPE: PRT
<213> ORGANISM: unknown
<220> FEATURE:
<223> OTHER INFORMATION: Ascaphine 5 Frog

<400> SEQUENCE: 52

Gly Ile Lys Asp Trp Ile Lys Gly Ala Ala Lys Lys Leu Ile Lys Thr
1               5                   10                  15

Val Ala Ser His Ile Ala Asn Gln
            20

<210> SEQ ID NO 53
<211> LENGTH: 22
<212> TYPE: PRT
<213> ORGANISM: unknown
<220> FEATURE:
<223> OTHER INFORMATION: Nigrocine 2 Frog

<400> SEQUENCE: 53

Gly Leu Leu Ser Lys Val Leu Gly Val Gly Lys Lys Val Leu Cys Gly
1               5                   10                  15

Val Ser Gly Leu Val Cys
            20

<210> SEQ ID NO 54
<211> LENGTH: 24
<212> TYPE: PRT
<213> ORGANISM: unknown
<220> FEATURE:
<223> OTHER INFORMATION: Pseudin 1 Rana Frog

<400> SEQUENCE: 54

Gly Leu Asn Thr Leu Lys Lys Val Phe Gln Gly Leu His Glu Ala Ile
1               5                   10                  15

Lys Leu Ile Asn Asn His Val Gln
            20

<210> SEQ ID NO 55
<211> LENGTH: 18
<212> TYPE: PRT
<213> ORGANISM: unknown
```

```
<220> FEATURE:
<223> OTHER INFORMATION: Ranalexin Frog

<400> SEQUENCE: 55

Phe Leu Gly Gly Leu Ile Val Pro Ala Met Ile Cys Ala Val Thr Lys
1               5                   10                  15

Lys Cys

<210> SEQ ID NO 56
<211> LENGTH: 26
<212> TYPE: PRT
<213> ORGANISM: unknown
<220> FEATURE:
<223> OTHER INFORMATION: Melittin bee

<400> SEQUENCE: 56

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 57
<211> LENGTH: 25
<212> TYPE: PRT
<213> ORGANISM: unknown
<220> FEATURE:
<223> OTHER INFORMATION: Lycotoxin 1 Spider

<400> SEQUENCE: 57

Ile Trp Leu Thr Ala Leu Lys Phe Leu Gly Lys His Ala Ala Lys Lys
1               5                   10                  15

Leu Ala Lys Gln Gln Leu Ser Lys Leu
            20                  25

<210> SEQ ID NO 58
<211> LENGTH: 19
<212> TYPE: PRT
<213> ORGANISM: unknown
<220> FEATURE:
<223> OTHER INFORMATION: Parasin 1 Fish

<400> SEQUENCE: 58

Lys Gly Arg Gly Lys Gln Gly Gly Lys Val Arg Ala Lys Ala Lys Thr
1               5                   10                  15

Arg Ser Ser

<210> SEQ ID NO 59
<211> LENGTH: 39
<212> TYPE: PRT
<213> ORGANISM: unknown
<220> FEATURE:
<223> OTHER INFORMATION: Buforin I Toad

<400> SEQUENCE: 59

Ala Gly Arg Gly Lys Gln Gly Gly Lys Val Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly Asn Tyr
        35

<210> SEQ ID NO 60
<211> LENGTH: 34
```

```
<212> TYPE: PRT
<213> ORGANISM: unknown
<220> FEATURE:
<223> OTHER INFORMATION: Dermaseptin 1 Frog

<400> SEQUENCE: 60

Ala Leu Trp Lys Thr Met Leu Lys Lys Leu Gly Thr Met Ala Leu His
1               5                   10                  15

Ala Gly Lys Ala Ala Leu Gly Ala Ala Ala Asp Thr Ile Ser Gln Gly
            20                  25                  30

Thr Gln

<210> SEQ ID NO 61
<211> LENGTH: 12
<212> TYPE: PRT
<213> ORGANISM: unknown
<220> FEATURE:
<223> OTHER INFORMATION: Bactenecin 1 Cow

<400> SEQUENCE: 61

Arg Leu Cys Arg Ile Val Val Ile Arg Val Cys Arg
1               5                   10

<210> SEQ ID NO 62
<211> LENGTH: 21
<212> TYPE: PRT
<213> ORGANISM: unknown
<220> FEATURE:
<223> OTHER INFORMATION: Thanatin Insect

<400> SEQUENCE: 62

Gly Ser Lys Lys Pro Val Pro Ile Ile Tyr Cys Asn Arg Arg Thr Gly
1               5                   10                  15

Lys Cys Gln Arg Met
            20

<210> SEQ ID NO 63
<211> LENGTH: 19
<212> TYPE: PRT
<213> ORGANISM: unknown
<220> FEATURE:
<223> OTHER INFORMATION: Brevinin 1T Rana frogs

<400> SEQUENCE: 63

Val Asn Pro Ile Ile Leu Gly Val Leu Pro Lys Val Cys Leu Ile Thr
1               5                   10                  15

Lys Lys Cys

<210> SEQ ID NO 64
<211> LENGTH: 26
<212> TYPE: PRT
<213> ORGANISM: unknown
<220> FEATURE:
<223> OTHER INFORMATION: Ranateurin 1 Rana frog

<400> SEQUENCE: 64

Ser Met Leu Ser Val Leu Lys Asn Leu Gly Lys Val Gly Leu Gly Phe
1               5                   10                  15

Val Ala Cys Lys Ile Asn Ile Lys Gln Cys
            20                  25

<210> SEQ ID NO 65
<211> LENGTH: 46
<212> TYPE: PRT
```

```
<213> ORGANISM: unknown
<220> FEATURE:
<223> OTHER INFORMATION: Esculentin 1 Rana frogs

<400> SEQUENCE: 65

Gly Ile Phe Ser Lys Leu Gly Arg Lys Lys Ile Lys Asn Leu Leu Ile
1               5                   10                  15

Ser Gly Leu Lys Asn Val Gly Lys Glu Val Gly Met Asp Val Val Arg
            20                  25                  30

Thr Gly Ile Lys Ile Ala Gly Cys Lys Ile Lys Gly Glu Cys
        35                  40                  45

<210> SEQ ID NO 66
<211> LENGTH: 17
<212> TYPE: PRT
<213> ORGANISM: Limulus polyphemus

<400> SEQUENCE: 66

Arg Trp Cys Phe Arg Val Cys Tyr Arg Gly Ile Cys Tyr Arg Lys Cys
1               5                   10                  15

Arg

<210> SEQ ID NO 67
<211> LENGTH: 25
<212> TYPE: PRT
<213> ORGANISM: unknown
<220> FEATURE:
<223> OTHER INFORMATION: Androctonin Scorpion

<400> SEQUENCE: 67

Arg Ser Val Cys Arg Gln Ile Lys Ile Cys Arg Arg Arg Gly Gly Cys
1               5                   10                  15

Tyr Tyr Lys Cys Thr Asn Arg Pro Tyr
            20                  25

<210> SEQ ID NO 68
<211> LENGTH: 30
<212> TYPE: PRT
<213> ORGANISM: Homo sapiens

<400> SEQUENCE: 68

Asp Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 69
<211> LENGTH: 38
<212> TYPE: PRT
<213> ORGANISM: unknown
<220> FEATURE:
<223> OTHER INFORMATION: beta-defensin cow

<400> SEQUENCE: 69

Asn Pro Val Ser Cys Val Arg Asn Lys Gly Ile Cys Val Pro Ile Arg
1               5                   10                  15

Cys Pro Gly Ser Met Lys Gln Ile Gly Thr Cys Val Gly Arg Ala Val
            20                  25                  30

Lys Cys Cys Arg Lys Lys
        35

<210> SEQ ID NO 70
```

<211> LENGTH: 18
<212> TYPE: PRT
<213> ORGANISM: unknown
<220> FEATURE:
<223> OTHER INFORMATION: theta-defensin monkey

<400> SEQUENCE: 70

Gly Phe Cys Arg Cys Leu Cys Arg Arg Gly Val Cys Arg Cys Ile Cys
1               5                   10                  15

Thr Arg

<210> SEQ ID NO 71
<211> LENGTH: 40
<212> TYPE: PRT
<213> ORGANISM: unknown
<220> FEATURE:
<223> OTHER INFORMATION: defensin (sapecin A) insect

<400> SEQUENCE: 71

Ala Thr Cys Asp Leu Leu Ser Gly Thr Gly Ile Asn His Ser Ala Cys
1               5                   10                  15

Ala Ala His Cys Leu Leu Arg Gly Asn Arg Gly Gly Tyr Cys Asn Gly
            20                  25                  30

Lys Ala Val Cys Val Cys Arg Asn
        35                  40

<210> SEQ ID NO 72
<211> LENGTH: 46
<212> TYPE: PRT
<213> ORGANISM: unknown
<220> FEATURE:
<223> OTHER INFORMATION: Thionin (crambin) plant

<400> SEQUENCE: 72

Thr Thr Cys Cys Pro Ser Ile Val Ala Arg Ser Asn Phe Asn Val Cys
1               5                   10                  15

Arg Ile Pro Gly Thr Pro Glu Ala Ile Cys Ala Thr Tyr Thr Gly Cys
            20                  25                  30

Ile Ile Ile Pro Gly Ala Thr Cys Pro Gly Asp Tyr Ala Asn
        35                  40                  45

<210> SEQ ID NO 73
<211> LENGTH: 50
<212> TYPE: PRT
<213> ORGANISM: unknown
<220> FEATURE:
<223> OTHER INFORMATION: defensin from radish

<400> SEQUENCE: 73

Gln Lys Leu Cys Gln Arg Pro Ser Gly Thr Trp Ser Gly Val Cys Gly
1               5                   10                  15

Asn Asn Asn Ala Cys Lys Asn Gln Cys Ile Arg Leu Glu Lys Ala Arg
            20                  25                  30

His Gly Ser Cys Asn Tyr Val Phe Pro Ala His Cys Ile Cys Tyr Phe
        35                  40                  45

Pro Cys
    50

<210> SEQ ID NO 74
<211> LENGTH: 44
<212> TYPE: PRT
<213> ORGANISM: Drosophila melanogaster -continued

```
<400> SEQUENCE: 74

Asp Cys Leu Ser Gly Arg Tyr Lys Gly Pro Cys Ala Val Trp Asp Asn
1               5                   10                  15

Glu Thr Cys Arg Arg Val Cys Lys Glu Glu Gly Arg Ser Ser Gly His
                20                  25                  30

Cys Ser Pro Ser Leu Lys Cys Trp Cys Glu Gly Cys
                35                  40

<210> SEQ ID NO 75
<211> LENGTH: 25
<212> TYPE: PRT
<213> ORGANISM: Homo sapiens

<400> SEQUENCE: 75

Asp Thr His Phe Pro Ile Cys Ile Phe Cys Cys Gly Cys Cys His Arg
1               5                   10                  15

Ser Lys Cys Gly Met Cys Cys Lys Thr
                20                  25

<210> SEQ ID NO 76
<211> LENGTH: 44
<212> TYPE: PRT
<213> ORGANISM: unknown
<220> FEATURE:
<223> OTHER INFORMATION: Bac 5 Cow

<400> SEQUENCE: 76

Arg Phe Arg Pro Pro Ile Arg Arg Pro Pro Ile Arg Pro Pro Phe Tyr
1               5                   10                  15

Pro Pro Phe Arg Pro Pro Ile Arg Pro Pro Ile Phe Pro Pro Ile Arg
                20                  25                  30

Pro Pro Phe Arg Pro Pro Leu Gly Arg Pro Phe Pro
                35                  40

<210> SEQ ID NO 77
<211> LENGTH: 39
<212> TYPE: PRT
<213> ORGANISM: unknown
<220> FEATURE:
<223> OTHER INFORMATION: PR-39 Pig

<400> SEQUENCE: 77

Arg Arg Arg Pro Arg Pro Pro Tyr Leu Pro Arg Pro Arg Pro Pro Pro
1               5                   10                  15

Phe Phe Pro Pro Arg Leu Pro Pro Arg Ile Pro Pro Gly Phe Pro Pro
                20                  25                  30

Arg Phe Pro Pro Arg Phe Pro
        35

<210> SEQ ID NO 78
<211> LENGTH: 20
<212> TYPE: PRT
<213> ORGANISM: unknown
<220> FEATURE:
<223> OTHER INFORMATION: Pyrrhocoricin Insect

<400> SEQUENCE: 78

Val Asp Lys Gly Ser Tyr Leu Pro Arg Pro Thr Pro Pro Arg Pro Ile
1               5                   10                  15

Tyr Asn Arg Asn
                20
```

<210> SEQ ID NO 79
<211> LENGTH: 24
<212> TYPE: PRT
<213> ORGANISM: Homo sapiens

<400> SEQUENCE: 79

Asp Ser His Ala Lys Arg His His Gly Tyr Lys Arg Lys Phe His Glu
1               5                   10                  15

Lys His His Ser His Arg Gly Tyr
            20

<210> SEQ ID NO 80
<211> LENGTH: 19
<212> TYPE: PRT
<213> ORGANISM: Unknown
<220> FEATURE:
<223> OTHER INFORMATION: ECP19

<400> SEQUENCE: 80

Arg Pro Pro Gln Phe Thr Arg Ala Gln Trp Phe Ala Ile Gln His Ile
1               5                   10                  15

Ser Leu Asn

<210> SEQ ID NO 81
<211> LENGTH: 23
<212> TYPE: PRT
<213> ORGANISM: Unknown
<220> FEATURE:
<223> OTHER INFORMATION: MSI-594

<400> SEQUENCE: 81

Gly Ile Gly Lys Phe Leu Lys Lys Ala Lys Lys Gly Ile Gly Ala Val
1               5                   10                  15

Leu Lys Val Leu Thr Thr Gly
            20

<210> SEQ ID NO 82
<211> LENGTH: 35
<212> TYPE: PRT
<213> ORGANISM: Unknown
<220> FEATURE:
<223> OTHER INFORMATION: TL-ColM

<400> SEQUENCE: 82

Met Glu Thr Leu Thr Val His Ala Pro Ser Pro Ser Thr Asn Leu Pro
1               5                   10                  15

Ser Tyr Gly Asn Gly Ala Phe Ser Leu Ser Ala Pro His Val Pro Gly
            20                  25                  30

Ala Gly Pro
        35

<210> SEQ ID NO 83
<211> LENGTH: 18
<212> TYPE: PRT
<213> ORGANISM: Unknown
<220> FEATURE:
<223> OTHER INFORMATION: SBO

<400> SEQUENCE: 83

Lys Leu Lys Lys Ile Ala Gln Lys Ile Lys Asn Phe Phe Ala Lys Leu
1               5                   10                  15

Val Ala

<210> SEQ ID NO 84
<211> LENGTH: 26
<212> TYPE: PRT
<213> ORGANISM: unknown
<220> FEATURE:
<223> OTHER INFORMATION: Macedocin

<400> SEQUENCE: 84

Gly Lys Asn Gly Val Phe Lys Thr Ile Ser His Glu Cys His Leu Asn
1               5                   10                  15

Thr Trp Ala Phe Leu Ala Thr Cys Cys Ser
            20                  25

<210> SEQ ID NO 85
<211> LENGTH: 22
<212> TYPE: PRT
<213> ORGANISM: unknown
<220> FEATURE:
<223> OTHER INFORMATION: Macedocin (Trunc)

<400> SEQUENCE: 85

Gly Lys Asn Gly Val Phe Lys Thr Ile Ser His Glu Cys His Leu Asn
1               5                   10                  15

Thr Trp Ala Phe Leu Ala
            20

<210> SEQ ID NO 86
<211> LENGTH: 28
<212> TYPE: PRT
<213> ORGANISM: unknown
<220> FEATURE:
<223> OTHER INFORMATION: D16

<400> SEQUENCE: 86

Ala Cys Lys Leu Lys Ser Leu Leu Lys Thr Leu Ser Lys Ala Lys Lys
1               5                   10                  15

Lys Lys Leu Lys Thr Leu Leu Lys Ala Leu Ser Lys
            20                  25

<210> SEQ ID NO 87
<211> LENGTH: 17
<212> TYPE: PRT
<213> ORGANISM: unknown
<220> FEATURE:
<223> OTHER INFORMATION: CPF-C1

<400> SEQUENCE: 87

Gly Phe Gly Ser Leu Leu Gly Lys Ala Leu Arg Leu Gly Ala Asn Val
1               5                   10                  15

Leu

<210> SEQ ID NO 88
<211> LENGTH: 34
<212> TYPE: PRT
<213> ORGANISM: unknown
<220> FEATURE:
<223> OTHER INFORMATION: TL-ColM

<400> SEQUENCE: 88

Glu Thr Leu Thr Val His Ala Pro Ser Pro Ser Thr Asn Leu Pro Ser
1               5                   10                  15

Tyr Gly Asn Gly Ala Phe Ser Leu Ser Ala Pro His Val Pro Gly Ala
            20                  25                  30

Gly Pro

<210> SEQ ID NO 89
<211> LENGTH: 26
<212> TYPE: PRT
<213> ORGANISM: unknown
<220> FEATURE:
<223> OTHER INFORMATION: TM-174E

<400> SEQUENCE: 89

Leu Ile Ser Lys Gly Trp Pro Tyr Leu Leu Val Val Leu Gly Ala
1               5                   10                  15

Thr Ile Tyr Phe Trp Gly Asn Ser Asn Gly
            20                  25

<210> SEQ ID NO 90
<211> LENGTH: 45
<212> TYPE: PRT
<213> ORGANISM: unknown
<220> FEATURE:
<223> OTHER INFORMATION: ECP45

<400> SEQUENCE: 90

Arg Pro Pro Gln Phe Thr Arg Ala Gln Trp Phe Ala Ile Gln His Ile
1               5                   10                  15

Ser Leu Asn Pro Pro Arg Cys Thr Ile Ala Met Arg Ala Ile Asn Asn
            20                  25                  30

Tyr Arg Trp Arg Cys Lys Asn Gln Asn Thr Phe Leu Arg
        35                  40                  45

<210> SEQ ID NO 91
<211> LENGTH: 50
<212> TYPE: PRT
<213> ORGANISM: unknown
<220> FEATURE:
<223> OTHER INFORMATION: ColicinE3_1-51 (S37F)

<400> SEQUENCE: 91

Ser Gly Gly Asp Gly Arg Gly His Asn Thr Gly Ala His Ser Thr Ser
1               5                   10                  15

Gly Asn Ile Asn Gly Gly Pro Thr Gly Leu Gly Val Gly Gly Gly Ala
            20                  25                  30

Ser Asp Gly Phe Gly Trp Ser Ser Glu Asn Asn Pro Trp Gly Gly Gly
        35                  40                  45

Ser Gly
    50

<210> SEQ ID NO 92
<211> LENGTH: 68
<212> TYPE: PRT
<213> ORGANISM: unknown
<220> FEATURE:
<223> OTHER INFORMATION: ColicinE3_1-69 (S37F)

<400> SEQUENCE: 92

Ser Gly Gly Asp Gly Arg Gly His Asn Thr Gly Ala His Ser Thr Ser
1               5                   10                  15

Gly Asn Ile Asn Gly Gly Pro Thr Gly Leu Gly Val Gly Gly Gly Ala
            20                  25                  30

Ser Asp Gly Phe Gly Trp Ser Ser Glu Asn Asn Pro Trp Gly Gly Gly
        35                  40                  45

Ser Gly Ser Gly Ile His Trp Gly Gly Gly Ser Gly His Gly Asn Gly

-continued

```
                50                  55                  60
Gly Gly Asn Gly
 65

<210> SEQ ID NO 93
<211> LENGTH: 52
<212> TYPE: PRT
<213> ORGANISM: unknown
<220> FEATURE:
<223> OTHER INFORMATION: ColicinD_1-53

<400> SEQUENCE: 93

Ser Asp Tyr Glu Gly Ser Gly Pro Thr Glu Gly Ile Asp Tyr Gly His
 1               5                  10                  15

Ser Met Val Val Trp Pro Ser Thr Gly Leu Ile Ser Gly Gly Asp Val
             20                  25                  30

Lys Pro Gly Gly Ser Ser Gly Ile Ala Pro Ser Met Pro Pro Gly Trp
         35                  40                  45

Gly Asp Tyr Ser
     50

<210> SEQ ID NO 94
<211> LENGTH: 7
<212> TYPE: PRT
<213> ORGANISM: Homo sapiens

<400> SEQUENCE: 94

His Pro Gln Tyr Asn Gln Arg
 1               5

<210> SEQ ID NO 95
<211> LENGTH: 34
<212> TYPE: PRT
<213> ORGANISM: Limulus polyphemus

<400> SEQUENCE: 95

Gly Phe Lys Leu Lys Gly Met Ala Arg Ile Ser Cys Leu Pro Asn Gly
 1               5                  10                  15

Gln Trp Ser Asn Phe Pro Pro Lys Cys Ile Arg Glu Cys Ala Met Val
             20                  25                  30

Ser Ser

<210> SEQ ID NO 96
<211> LENGTH: 18
<212> TYPE: PRT
<213> ORGANISM: artificial
<220> FEATURE:
<223> OTHER INFORMATION: synthetic sequence

<400> SEQUENCE: 96

Gly Phe Phe Ile Pro Ala Val Ile Leu Pro Ser Ile Ala Phe Leu Ile
 1               5                  10                  15

Val Pro

<210> SEQ ID NO 97
<211> LENGTH: 5
<212> TYPE: PRT
<213> ORGANISM: artificial
<220> FEATURE:
<223> OTHER INFORMATION: synthetic sequence

<400> SEQUENCE: 97
```

-continued

Phe Phe Val Ala Pro
1               5

<210> SEQ ID NO 98
<211> LENGTH: 13
<212> TYPE: PRT
<213> ORGANISM: unknown
<220> FEATURE:
<223> OTHER INFORMATION: alpha4-helix of T4 lysozyme

<400> SEQUENCE: 98

Pro Asn Arg Ala Lys Arg Val Ile Thr Thr Phe Arg Thr
1               5                   10

<210> SEQ ID NO 99
<211> LENGTH: 27
<212> TYPE: PRT
<213> ORGANISM: artificial
<220> FEATURE:
<223> OTHER INFORMATION: synthetic sequence

<400> SEQUENCE: 99

Lys Arg Trp Val Lys Arg Val Lys Arg Val Lys Arg Trp Val Lys Arg
1               5                   10                  15

Val Val Arg Val Val Lys Arg Trp Val Lys Arg
            20                  25

<210> SEQ ID NO 100
<211> LENGTH: 25
<212> TYPE: PRT
<213> ORGANISM: Artificial Sequence
<220> FEATURE:
<223> OTHER INFORMATION: synthetic sequence; MW2

<400> SEQUENCE: 100

Gly Lys Pro Gly Trp Leu Ile Lys Val Ala Leu Lys Phe Lys Lys Leu
1               5                   10                  15

Ile Arg Arg Pro Leu Lys Arg Leu Ala
            20                  25

<210> SEQ ID NO 101
<211> LENGTH: 6
<212> TYPE: PRT
<213> ORGANISM: artificial sequence
<220> FEATURE:
<223> OTHER INFORMATION: His-Tag (6x)

<400> SEQUENCE: 101

His His His His His His
1               5

<210> SEQ ID NO 102
<211> LENGTH: 430
<212> TYPE: PRT
<213> ORGANISM: artificial sequence
<220> FEATURE:
<223> OTHER INFORMATION: Fusion protein comprising CHAP domain of LysK
      endolysin, M23 endopeptidase domain of lysostaphin, cell wall
      binding domain of ALE-1, and His6-tag; w/o N-terminal methionine

<400> SEQUENCE: 102

Ala Lys Thr Gln Ala Glu Ile Asn Lys Arg Leu Asp Ala Tyr Ala Lys
1               5                   10                  15

Gly Thr Val Asp Ser Pro Tyr Arg Val Lys Lys Ala Thr Ser Tyr Asp
            20                  25                  30

-continued

Pro Ser Phe Gly Val Met Glu Ala Gly Ala Ile Asp Ala Asp Gly Tyr
         35                  40                  45

Tyr His Ala Gln Cys Gln Asp Leu Ile Thr Asp Tyr Val Leu Trp Leu
 50                  55                  60

Thr Asp Asn Lys Val Arg Thr Trp Gly Asn Ala Lys Asp Gln Ile Lys
 65                  70                  75                  80

Gln Ser Tyr Gly Thr Gly Phe Lys Ile His Glu Asn Lys Pro Ser Thr
                 85                  90                  95

Val Pro Lys Lys Gly Trp Ile Ala Val Phe Thr Ser Gly Ser Tyr Glu
             100                 105                 110

Gln Trp Gly His Ile Gly Ile Val Tyr Asp Gly Gly Asn Thr Ser Thr
         115                 120                 125

Phe Thr Ile Leu Glu Gln Asn Trp Asn Gly Tyr Ala Asn Lys Lys Pro
130                 135                 140

Thr Lys Arg Val Asp Asn Tyr Tyr Gly Leu Thr His Phe Ile Glu Ile
145                 150                 155                 160

Pro Val Lys Ala Gly Thr Thr Val Lys Lys Glu Thr Ala Lys Lys Ser
                165                 170                 175

Ala Thr Ser His Glu His Ser Ala Gln Trp Leu Asn Asn Tyr Lys Lys
            180                 185                 190

Gly Tyr Gly Tyr Gly Pro Tyr Pro Leu Gly Ile Asn Gly Gly Met His
        195                 200                 205

Tyr Gly Val Asp Phe Phe Met Asn Ile Gly Thr Pro Val Lys Ala Ile
    210                 215                 220

Ser Ser Gly Lys Ile Val Glu Ala Gly Trp Ser Asn Tyr Gly Gly Gly
225                 230                 235                 240

Asn Gln Ile Gly Leu Ile Glu Asn Asp Gly Val His Arg Gln Trp Tyr
                245                 250                 255

Met His Leu Ser Lys Tyr Asn Val Lys Val Gly Asp Tyr Val Lys Ala
            260                 265                 270

Gly Gln Ile Ile Gly Trp Ser Gly Ser Thr Gly Tyr Ser Thr Ala Pro
        275                 280                 285

His Leu His Phe Gln Arg Met Val Asn Ser Phe Ser Asn Ser Thr Ala
    290                 295                 300

Gln Asp Pro Met Pro Phe Leu Lys Ser Ala Gly Tyr Gly Lys Ala Gly
305                 310                 315                 320

Gly Thr Val Thr Pro Thr Pro Asn Pro Gly Asn Gly Tyr Lys Thr Asn
                325                 330                 335

Lys Tyr Gly Thr Leu Tyr Lys Ser Glu Ser Ala Ser Phe Thr Ala Asn
            340                 345                 350

Thr Asp Ile Ile Thr Arg Leu Thr Gly Pro Phe Arg Ser Met Pro Gln
        355                 360                 365

Ser Gly Val Leu Arg Lys Gly Leu Thr Ile Lys Tyr Asp Glu Val Met
370                 375                 380

Lys Gln Asp Gly His Val Trp Val Gly Tyr Asn Thr Asn Ser Gly Lys
385                 390                 395                 400

Arg Val Tyr Leu Pro Val Arg Thr Trp Asn Glu Ser Thr Gly Glu Leu
                405                 410                 415

Gly Pro Leu Trp Gly Thr Ile Lys His His His His
            420                 425                 430

<210> SEQ ID NO 103
<211> LENGTH: 432
<212> TYPE: PRT

<213> ORGANISM: artificial sequence
<220> FEATURE:
<223> OTHER INFORMATION: Fusion protein comprising CHAP domain of LysK
      endolysin, M23 endopeptidase domain of lysostaphin, cell wall
      binding domain of ALE-1, and His6-tag via GS linker; w/o
      N-terminal methionine

<400> SEQUENCE: 103

```
Ala Lys Thr Gln Ala Glu Ile Asn Lys Arg Leu Asp Ala Tyr Ala Lys
1               5                   10                  15

Gly Thr Val Asp Ser Pro Tyr Arg Val Lys Lys Ala Thr Ser Tyr Asp
                20                  25                  30

Pro Ser Phe Gly Val Met Glu Ala Gly Ala Ile Asp Ala Asp Gly Tyr
            35                  40                  45

Tyr His Ala Gln Cys Gln Asp Leu Ile Thr Asp Tyr Val Leu Trp Leu
        50                  55                  60

Thr Asp Asn Lys Val Arg Thr Trp Gly Asn Ala Lys Asp Gln Ile Lys
65                  70                  75                  80

Gln Ser Tyr Gly Thr Gly Phe Lys Ile His Glu Asn Lys Pro Ser Thr
                85                  90                  95

Val Pro Lys Lys Gly Trp Ile Ala Val Phe Thr Ser Gly Ser Tyr Glu
            100                 105                 110

Gln Trp Gly His Ile Gly Ile Val Tyr Asp Gly Gly Asn Thr Ser Thr
        115                 120                 125

Phe Thr Ile Leu Glu Gln Asn Trp Asn Gly Tyr Ala Asn Lys Lys Pro
    130                 135                 140

Thr Lys Arg Val Asp Asn Tyr Tyr Gly Leu Thr His Phe Ile Glu Ile
145                 150                 155                 160

Pro Val Lys Ala Gly Thr Thr Val Lys Lys Glu Thr Ala Lys Lys Ser
                165                 170                 175

Ala Thr Ser His Glu His Ser Ala Gln Trp Leu Asn Asn Tyr Lys Lys
            180                 185                 190

Gly Tyr Gly Tyr Gly Pro Tyr Pro Leu Gly Ile Asn Gly Gly Met His
        195                 200                 205

Tyr Gly Val Asp Phe Phe Met Asn Ile Gly Thr Pro Val Lys Ala Ile
    210                 215                 220

Ser Ser Gly Lys Ile Val Glu Ala Gly Trp Ser Asn Tyr Gly Gly Gly
225                 230                 235                 240

Asn Gln Ile Gly Leu Ile Glu Asn Asp Gly Val His Arg Gln Trp Tyr
                245                 250                 255

Met His Leu Ser Lys Tyr Asn Val Lys Val Gly Asp Tyr Val Lys Ala
            260                 265                 270

Gly Gln Ile Ile Gly Trp Ser Gly Ser Thr Gly Tyr Ser Thr Ala Pro
        275                 280                 285

His Leu His Phe Gln Arg Met Val Asn Ser Phe Ser Asn Ser Thr Ala
    290                 295                 300

Gln Asp Pro Met Pro Phe Leu Lys Ser Ala Gly Tyr Gly Lys Ala Gly
305                 310                 315                 320

Gly Thr Val Thr Pro Thr Pro Asn Pro Gly Asn Gly Tyr Lys Thr Asn
                325                 330                 335

Lys Tyr Gly Thr Leu Tyr Lys Ser Glu Ser Ala Ser Phe Thr Ala Asn
            340                 345                 350

Thr Asp Ile Ile Thr Arg Leu Thr Gly Pro Phe Arg Ser Met Pro Gln
        355                 360                 365

Ser Gly Val Leu Arg Lys Gly Leu Thr Ile Lys Tyr Asp Glu Val Met
```

```
            370                 375                 380
Lys Gln Asp Gly His Val Trp Val Gly Tyr Asn Thr Asn Ser Gly Lys
385                 390                 395                 400

Arg Val Tyr Leu Pro Val Arg Thr Trp Asn Glu Ser Thr Gly Glu Leu
                405                 410                 415

Gly Pro Leu Trp Gly Thr Ile Lys Gly Ser His His His His His His
                420                 425                 430
```

<210> SEQ ID NO 104
<211> LENGTH: 439
<212> TYPE: PRT
<213> ORGANISM: artificial sequence
<220> FEATURE:
<223> OTHER INFORMATION: Fusion protein comprising CHAP domain of LysK
      endolysin, M23 endopeptidase domain of lysostaphin, cell wall
      binding domain of ALE-1, His6-tag and synthetic peptide HPQYNQR;
      w/o N-terminal methionine

<400> SEQUENCE: 104

```
Ala Lys Thr Gln Ala Glu Ile Asn Lys Arg Leu Asp Ala Tyr Ala Lys
1               5                   10                  15

Gly Thr Val Asp Ser Pro Tyr Arg Val Lys Lys Ala Thr Ser Tyr Asp
                20                  25                  30

Pro Ser Phe Gly Val Met Glu Ala Gly Ala Ile Asp Ala Asp Gly Tyr
            35                  40                  45

Tyr His Ala Gln Cys Gln Asp Leu Ile Thr Asp Tyr Val Leu Trp Leu
50                  55                  60

Thr Asp Asn Lys Val Arg Thr Trp Gly Asn Ala Lys Asp Gln Ile Lys
65                  70                  75                  80

Gln Ser Tyr Gly Thr Gly Phe Lys Ile His Glu Asn Lys Pro Ser Thr
                85                  90                  95

Val Pro Lys Lys Gly Trp Ile Ala Val Phe Thr Ser Gly Ser Tyr Glu
                100                 105                 110

Gln Trp Gly His Ile Gly Ile Val Tyr Asp Gly Gly Asn Thr Ser Thr
            115                 120                 125

Phe Thr Ile Leu Glu Gln Asn Trp Asn Gly Tyr Ala Asn Lys Lys Pro
130                 135                 140

Thr Lys Arg Val Asp Asn Tyr Tyr Gly Leu Thr His Phe Ile Glu Ile
145                 150                 155                 160

Pro Val Lys Ala Gly Thr Thr Val Lys Lys Glu Thr Ala Lys Lys Ser
                165                 170                 175

Ala Thr Ser His Glu His Ser Ala Gln Trp Leu Asn Asn Tyr Lys Lys
            180                 185                 190

Gly Tyr Gly Tyr Gly Pro Tyr Pro Leu Gly Ile Asn Gly Gly Met His
            195                 200                 205

Tyr Gly Val Asp Phe Phe Met Asn Ile Gly Thr Pro Val Lys Ala Ile
210                 215                 220

Ser Ser Gly Lys Ile Val Glu Ala Gly Trp Ser Asn Tyr Gly Gly Gly
225                 230                 235                 240

Asn Gln Ile Gly Leu Ile Glu Asn Asp Gly Val His Arg Gln Trp Tyr
                245                 250                 255

Met His Leu Ser Lys Tyr Asn Val Lys Val Gly Asp Tyr Val Lys Ala
            260                 265                 270

Gly Gln Ile Ile Gly Trp Ser Gly Ser Thr Gly Tyr Ser Thr Ala Pro
            275                 280                 285

His Leu His Phe Gln Arg Met Val Asn Ser Phe Ser Asn Ser Thr Ala
```

```
                290                 295                 300
Gln Asp Pro Met Pro Phe Leu Lys Ser Ala Gly Tyr Gly Lys Ala Gly
305                 310                 315                 320

Gly Thr Val Thr Pro Thr Pro Asn Pro Gly Asn Gly Tyr Lys Thr Asn
                325                 330                 335

Lys Tyr Gly Thr Leu Tyr Lys Ser Glu Ser Ala Ser Phe Thr Ala Asn
                340                 345                 350

Thr Asp Ile Ile Thr Arg Leu Thr Gly Pro Phe Arg Ser Met Pro Gln
                355                 360                 365

Ser Gly Val Leu Arg Lys Gly Leu Thr Ile Lys Tyr Asp Glu Val Met
            370                 375                 380

Lys Gln Asp Gly His Val Trp Val Gly Tyr Asn Thr Asn Ser Gly Lys
385                 390                 395                 400

Arg Val Tyr Leu Pro Val Arg Thr Trp Asn Glu Ser Thr Gly Glu Leu
                405                 410                 415

Gly Pro Leu Trp Gly Thr Ile Lys His His His His His His Leu Lys
            420                 425                 430

His Pro Gln Tyr Asn Gln Arg
            435

<210> SEQ ID NO 105
<211> LENGTH: 440
<212> TYPE: PRT
<213> ORGANISM: artificial sequence
<220> FEATURE:
<223> OTHER INFORMATION: Fusion protein comprising CHAP domain of LysK
      endolysin, M23 endopeptidase domain of lysostaphin, cell wall
      binding domain of ALE-1, His6-tag and synthetic peptide HPQYNQR

<400> SEQUENCE: 105

Met Ala Lys Thr Gln Ala Glu Ile Asn Lys Arg Leu Asp Ala Tyr Ala
1               5                   10                  15

Lys Gly Thr Val Asp Ser Pro Tyr Arg Val Lys Lys Ala Thr Ser Tyr
                20                  25                  30

Asp Pro Ser Phe Gly Val Met Glu Ala Gly Ala Ile Asp Ala Asp Gly
            35                  40                  45

Tyr Tyr His Ala Gln Cys Gln Asp Leu Ile Thr Asp Tyr Val Leu Trp
    50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
            100                 105                 110

Glu Gln Trp Gly His Ile Gly Ile Val Tyr Asp Gly Asn Thr Ser
            115                 120                 125

Thr Phe Thr Ile Leu Glu Gln Asn Trp Asn Gly Tyr Ala Asn Lys Lys
            130                 135                 140

Pro Thr Lys Arg Val Asp Asn Tyr Tyr Gly Leu Thr His Phe Ile Glu
145                 150                 155                 160

Ile Pro Val Lys Ala Gly Thr Thr Val Lys Lys Glu Thr Ala Lys Lys
                165                 170                 175

Ser Ala Thr Ser His Glu His Ser Ala Gln Trp Leu Asn Asn Tyr Lys
            180                 185                 190

Lys Gly Tyr Gly Tyr Gly Pro Tyr Pro Leu Gly Ile Asn Gly Gly Met
            195                 200                 205
```

His Tyr Gly Val Asp Phe Phe Met Asn Ile Gly Thr Pro Val Lys Ala
    210                 215                 220

Ile Ser Ser Gly Lys Ile Val Glu Ala Gly Trp Ser Asn Tyr Gly Gly
225                 230                 235                 240

Gly Asn Gln Ile Gly Leu Ile Glu Asn Asp Gly Val His Arg Gln Trp
                245                 250                 255

Tyr Met His Leu Ser Lys Tyr Asn Val Lys Val Gly Asp Tyr Val Lys
            260                 265                 270

Ala Gly Gln Ile Ile Gly Trp Ser Gly Ser Thr Gly Tyr Ser Thr Ala
        275                 280                 285

Pro His Leu His Phe Gln Arg Met Val Asn Ser Phe Ser Asn Ser Thr
    290                 295                 300

Ala Gln Asp Pro Met Pro Phe Leu Lys Ser Ala Gly Tyr Gly Lys Ala
305                 310                 315                 320

Gly Gly Thr Val Thr Pro Thr Pro Asn Pro Gly Asn Gly Tyr Lys Thr
                325                 330                 335

Asn Lys Tyr Gly Thr Leu Tyr Lys Ser Glu Ser Ala Ser Phe Thr Ala
            340                 345                 350

Asn Thr Asp Ile Ile Thr Arg Leu Thr Gly Pro Phe Arg Ser Met Pro
        355                 360                 365

Gln Ser Gly Val Leu Arg Lys Gly Leu Thr Ile Lys Tyr Asp Glu Val
    370                 375                 380

Met Lys Gln Asp Gly His Val Trp Val Gly Tyr Asn Thr Asn Ser Gly
385                 390                 395                 400

Lys Arg Val Tyr Leu Pro Val Arg Thr Trp Asn Glu Ser Thr Gly Glu
                405                 410                 415

Leu Gly Pro Leu Trp Gly Thr Ile Lys His His His His His His Leu
            420                 425                 430

Lys His Pro Gln Tyr Asn Gln Arg
        435                 440

<210> SEQ ID NO 106
<211> LENGTH: 438
<212> TYPE: PRT
<213> ORGANISM: Artificial sequence
<220> FEATURE:
<223> OTHER INFORMATION: Fusion protein comprising CHAP domain of LysK
      endolysin, M23 endopeptidase domain of lysostaphin, cell wall
      binding domain of ALE-1, His6-tag and synthetic peptide KNK; w/o
      N-terminal methionine

<400> SEQUENCE: 106

Ala Lys Thr Gln Ala Glu Ile Asn Lys Arg Leu Asp Ala Tyr Ala Lys
1               5                   10                  15

Gly Thr Val Asp Ser Pro Tyr Arg Val Lys Lys Ala Thr Ser Tyr Asp
            20                  25                  30

Pro Ser Phe Gly Val Met Glu Ala Gly Ala Ile Asp Ala Asp Gly Tyr
        35                  40                  45

Tyr His Ala Gln Cys Gln Asp Leu Ile Thr Asp Tyr Val Leu Trp Leu
    50                  55                  60

Thr Asp Asn Lys Val Arg Thr Trp Gly Asn Ala Lys Asp Gln Ile Lys
65                  70                  75                  80

Gln Ser Tyr Gly Thr Gly Phe Lys Ile His Glu Asn Lys Pro Ser Thr
                85                  90                  95

Val Pro Lys Lys Gly Trp Ile Ala Val Phe Thr Ser Gly Ser Tyr Glu
            100                 105                 110

Gln Trp Gly His Ile Gly Ile Val Tyr Asp Gly Gly Asn Thr Ser Thr
            115                 120                 125

Phe Thr Ile Leu Glu Gln Asn Trp Asn Gly Tyr Ala Asn Lys Lys Pro
        130                 135                 140

Thr Lys Arg Val Asp Asn Tyr Tyr Gly Leu Thr His Phe Ile Glu Ile
145                 150                 155                 160

Pro Val Lys Ala Gly Thr Thr Val Lys Lys Glu Thr Ala Lys Lys Ser
                165                 170                 175

Ala Thr Ser His Glu His Ser Ala Gln Trp Leu Asn Asn Tyr Lys Lys
            180                 185                 190

Gly Tyr Gly Tyr Gly Pro Tyr Pro Leu Gly Ile Asn Gly Gly Met His
        195                 200                 205

Tyr Gly Val Asp Phe Phe Met Asn Ile Gly Thr Pro Val Lys Ala Ile
    210                 215                 220

Ser Ser Gly Lys Ile Val Glu Ala Gly Trp Ser Asn Tyr Gly Gly Gly
225                 230                 235                 240

Asn Gln Ile Gly Leu Ile Glu Asn Asp Gly Val His Arg Gln Trp Tyr
                245                 250                 255

Met His Leu Ser Lys Tyr Asn Val Lys Val Gly Asp Tyr Val Lys Ala
            260                 265                 270

Gly Gln Ile Ile Gly Trp Ser Gly Ser Thr Gly Tyr Ser Thr Ala Pro
        275                 280                 285

His Leu His Phe Gln Arg Met Val Asn Ser Phe Ser Asn Ser Thr Ala
    290                 295                 300

Gln Asp Pro Met Pro Phe Leu Lys Ser Ala Gly Tyr Gly Lys Ala Gly
305                 310                 315                 320

Gly Thr Val Thr Pro Thr Pro Asn Pro Gly Asn Gly Tyr Lys Thr Asn
                325                 330                 335

Lys Tyr Gly Thr Leu Tyr Lys Ser Glu Ser Ala Ser Phe Thr Ala Asn
            340                 345                 350

Thr Asp Ile Ile Thr Arg Leu Thr Gly Pro Phe Arg Ser Met Pro Gln
        355                 360                 365

Ser Gly Val Leu Arg Lys Gly Leu Thr Ile Lys Tyr Asp Glu Val Met
    370                 375                 380

Lys Gln Asp Gly His Val Trp Val Gly Tyr Asn Thr Asn Ser Gly Lys
385                 390                 395                 400

Arg Val Tyr Leu Pro Val Arg Thr Trp Asn Glu Ser Thr Gly Glu Leu
                405                 410                 415

Gly Pro Leu Trp Gly Thr Ile Lys Gly Ser His His His His His His
            420                 425                 430

Gly Gly Ser Lys Asn Lys
        435

<210> SEQ ID NO 107
<211> LENGTH: 439
<212> TYPE: PRT
<213> ORGANISM: Artificial sequence
<220> FEATURE:
<223> OTHER INFORMATION: Fusion protein comprising CHAP domain of LysK
      endolysin, M23 endopeptidase domain of lysostaphin, cell wall
      binding domain of ALE-1, His6-tag and synthetic peptide KNK

<400> SEQUENCE: 107

Met Ala Lys Thr Gln Ala Glu Ile Asn Lys Arg Leu Asp Ala Tyr Ala
1               5                   10                  15

```
Lys Gly Thr Val Asp Ser Pro Tyr Arg Val Lys Lys Ala Thr Ser Tyr
             20                  25                  30
Asp Pro Ser Phe Gly Val Met Glu Ala Gly Ala Ile Asp Ala Asp Gly
             35                  40                  45
Tyr Tyr His Ala Gln Cys Gln Asp Leu Ile Thr Asp Tyr Val Leu Trp
         50                  55                  60
Leu Thr Asp Asn Lys Val Arg Thr Trp Gly Asn Ala Lys Asp Gln Ile
 65                  70                  75                  80
Lys Gln Ser Tyr Gly Thr Gly Phe Lys Ile His Glu Asn Lys Pro Ser
                 85                  90                  95
Thr Val Pro Lys Lys Gly Trp Ile Ala Val Phe Thr Ser Gly Ser Tyr
             100                 105                 110
Glu Gln Trp Gly His Ile Gly Ile Val Tyr Asp Gly Gly Asn Thr Ser
             115                 120                 125
Thr Phe Thr Ile Leu Glu Gln Asn Trp Asn Gly Tyr Ala Asn Lys Lys
         130                 135                 140
Pro Thr Lys Arg Val Asp Asn Tyr Tyr Gly Leu Thr His Phe Ile Glu
145                 150                 155                 160
Ile Pro Val Lys Ala Gly Thr Thr Val Lys Lys Glu Thr Ala Lys Lys
                 165                 170                 175
Ser Ala Thr Ser His Glu His Ser Ala Gln Trp Leu Asn Asn Tyr Lys
             180                 185                 190
Lys Gly Tyr Gly Tyr Gly Pro Tyr Pro Leu Gly Ile Asn Gly Gly Met
             195                 200                 205
His Tyr Gly Val Asp Phe Phe Met Asn Ile Gly Thr Pro Val Lys Ala
210                 215                 220
Ile Ser Ser Gly Lys Ile Val Glu Ala Gly Trp Ser Asn Tyr Gly Gly
225                 230                 235                 240
Gly Asn Gln Ile Gly Leu Ile Glu Asn Asp Gly Val His Arg Gln Trp
             245                 250                 255
Tyr Met His Leu Ser Lys Tyr Asn Val Lys Val Gly Asp Tyr Val Lys
             260                 265                 270
Ala Gly Gln Ile Ile Gly Trp Ser Gly Ser Thr Gly Tyr Ser Thr Ala
             275                 280                 285
Pro His Leu His Phe Gln Arg Met Val Asn Ser Phe Ser Asn Ser Thr
290                 295                 300
Ala Gln Asp Pro Met Pro Phe Leu Lys Ser Ala Gly Tyr Gly Lys Ala
305                 310                 315                 320
Gly Gly Thr Val Thr Pro Thr Pro Asn Pro Gly Asn Gly Tyr Lys Thr
             325                 330                 335
Asn Lys Tyr Gly Thr Leu Tyr Lys Ser Glu Ser Ala Ser Phe Thr Ala
             340                 345                 350
Asn Thr Asp Ile Ile Thr Arg Leu Thr Gly Pro Phe Arg Ser Met Pro
         355                 360                 365
Gln Ser Gly Val Leu Arg Lys Gly Leu Thr Ile Lys Tyr Asp Glu Val
     370                 375                 380
Met Lys Gln Asp Gly His Val Trp Val Gly Tyr Asn Thr Asn Ser Gly
385                 390                 395                 400
Lys Arg Val Tyr Leu Pro Val Arg Thr Trp Asn Glu Ser Thr Gly Glu
                 405                 410                 415
Leu Gly Pro Leu Trp Gly Thr Ile Lys Gly Ser His His His His
             420                 425                 430
His Gly Gly Ser Lys Asn Lys
```

435

<210> SEQ ID NO 108
<211> LENGTH: 438
<212> TYPE: PRT
<213> ORGANISM: Artificial sequence
<220> FEATURE:
<223> OTHER INFORMATION: Fusion protein comprising CHAP domain of LysK
      endolysin, M23 endopeptidase domain of lysostaphin, cell wall
      binding domain of ALE-1, His6-tag and synthetic peptide KNK; incl.
      mutations K17E and H51Q; w/o N-terminal methionine

<400> SEQUENCE: 108

Ala Lys Thr Gln Ala Glu Ile Asn Lys Arg Leu Asp Ala Tyr Ala Glu
1               5                   10                  15

Gly Thr Val Asp Ser Pro Tyr Arg Val Lys Lys Ala Thr Ser Tyr Asp
            20                  25                  30

Pro Ser Phe Gly Val Met Glu Ala Gly Ala Ile Asp Ala Asp Gly Tyr
        35                  40                  45

Tyr Gln Ala Gln Cys Gln Asp Leu Ile Thr Asp Tyr Val Leu Trp Leu
    50                  55                  60

Thr Asp Asn Lys Val Arg Thr Trp Gly Asn Ala Lys Asp Gln Ile Lys
65                  70                  75                  80

Gln Ser Tyr Gly Thr Gly Phe Lys Ile His Glu Asn Lys Pro Ser Thr
                85                  90                  95

Val Pro Lys Lys Gly Trp Ile Ala Val Phe Thr Ser Gly Ser Tyr Glu
            100                 105                 110

Gln Trp Gly His Ile Gly Ile Val Tyr Asp Gly Gly Asn Thr Ser Thr
        115                 120                 125

Phe Thr Ile Leu Glu Gln Asn Trp Asn Gly Tyr Ala Asn Lys Lys Pro
    130                 135                 140

Thr Lys Arg Val Asp Asn Tyr Tyr Gly Leu Thr His Phe Ile Glu Ile
145                 150                 155                 160

Pro Val Lys Ala Gly Thr Thr Val Lys Lys Glu Thr Ala Lys Lys Ser
                165                 170                 175

Ala Thr Ser His Glu His Ser Ala Gln Trp Leu Asn Asn Tyr Lys Lys
            180                 185                 190

Gly Tyr Gly Tyr Gly Pro Tyr Pro Leu Gly Ile Asn Gly Gly Met His
        195                 200                 205

Tyr Gly Val Asp Phe Phe Met Asn Ile Gly Thr Pro Val Lys Ala Ile
    210                 215                 220

Ser Ser Gly Lys Ile Val Glu Ala Gly Trp Ser Asn Tyr Gly Gly Gly
225                 230                 235                 240

Asn Gln Ile Gly Leu Ile Glu Asn Asp Gly Val His Arg Gln Trp Tyr
                245                 250                 255

Met His Leu Ser Lys Tyr Asn Val Lys Val Gly Asp Tyr Val Lys Ala
            260                 265                 270

Gly Gln Ile Ile Gly Trp Ser Gly Ser Thr Gly Tyr Ser Thr Ala Pro
        275                 280                 285

His Leu His Phe Gln Arg Met Val Asn Ser Phe Ser Asn Ser Thr Ala
    290                 295                 300

Gln Asp Pro Met Pro Phe Leu Lys Ser Ala Gly Tyr Gly Lys Ala Gly
305                 310                 315                 320

Gly Thr Val Thr Pro Thr Pro Asn Pro Gly Asn Gly Tyr Lys Thr Asn
                325                 330                 335

Lys Tyr Gly Thr Leu Tyr Lys Ser Glu Ser Ala Ser Phe Thr Ala Asn

```
                  340                 345                 350
Thr Asp Ile Ile Thr Arg Leu Thr Gly Pro Phe Arg Ser Met Pro Gln
                355                 360                 365

Ser Gly Val Leu Arg Lys Gly Leu Thr Ile Lys Tyr Asp Glu Val Met
    370                 375                 380

Lys Gln Asp Gly His Val Trp Val Gly Tyr Asn Thr Asn Ser Gly Lys
385                 390                 395                 400

Arg Val Tyr Leu Pro Val Arg Thr Trp Asn Glu Ser Thr Gly Glu Leu
                405                 410                 415

Gly Pro Leu Trp Gly Thr Ile Lys Gly Ser His His His His His His
            420                 425                 430

Gly Gly Ser Lys Asn Lys
            435

<210> SEQ ID NO 109
<211> LENGTH: 439
<212> TYPE: PRT
<213> ORGANISM: Artificial Sequence
<220> FEATURE:
<223> OTHER INFORMATION: Fusion protein comprising CHAP domain of LysK
      endolysin, M23 endopeptidase domain of lysostaphin, cell wall
      binding domain of ALE-1, His6-tag and synthetic peptide KNK; incl.
      mutations K17E and H51Q

<400> SEQUENCE: 109

Met Ala Lys Thr Gln Ala Glu Ile Asn Lys Arg Leu Asp Ala Tyr Ala
1               5                   10                  15

Glu Gly Thr Val Asp Ser Pro Tyr Arg Val Lys Lys Ala Thr Ser Tyr
                20                  25                  30

Asp Pro Ser Phe Gly Val Met Glu Ala Gly Ala Ile Asp Ala Asp Gly
            35                  40                  45

Tyr Tyr Gln Ala Gln Cys Gln Asp Leu Ile Thr Asp Tyr Val Leu Trp
        50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
            100                 105                 110

Glu Gln Trp Gly His Ile Gly Ile Val Tyr Asp Gly Gly Asn Thr Ser
        115                 120                 125

Thr Phe Thr Ile Leu Glu Gln Asn Trp Asn Gly Tyr Ala Asn Lys Lys
    130                 135                 140

Pro Thr Lys Arg Val Asp Asn Tyr Tyr Gly Leu Thr His Phe Ile Glu
145                 150                 155                 160

Ile Pro Val Lys Ala Gly Thr Thr Val Lys Lys Glu Thr Ala Lys Lys
                165                 170                 175

Ser Ala Thr Ser His Glu His Ser Ala Gln Trp Leu Asn Asn Tyr Lys
            180                 185                 190

Lys Gly Tyr Gly Tyr Gly Pro Tyr Pro Leu Gly Ile Asn Gly Gly Met
        195                 200                 205

His Tyr Gly Val Asp Phe Phe Met Asn Ile Gly Thr Pro Val Lys Ala
    210                 215                 220

Ile Ser Ser Gly Lys Ile Val Glu Ala Gly Trp Ser Asn Tyr Gly Gly
225                 230                 235                 240

Gly Asn Gln Ile Gly Leu Ile Glu Asn Asp Gly Val His Arg Gln Trp
```

```
                    245                 250                 255
Tyr Met His Leu Ser Lys Tyr Asn Val Lys Val Gly Asp Tyr Val Lys
        260                 265                 270

Ala Gly Gln Ile Ile Gly Trp Ser Gly Ser Thr Gly Tyr Ser Thr Ala
            275                 280                 285

Pro His Leu His Phe Gln Arg Met Val Asn Ser Phe Ser Asn Ser Thr
        290                 295                 300

Ala Gln Asp Pro Met Pro Phe Leu Lys Ser Ala Gly Tyr Gly Lys Ala
305                 310                 315                 320

Gly Gly Thr Val Thr Pro Thr Pro Asn Pro Gly Asn Gly Tyr Lys Thr
                325                 330                 335

Asn Lys Tyr Gly Thr Leu Tyr Lys Ser Glu Ser Ala Ser Phe Thr Ala
            340                 345                 350

Asn Thr Asp Ile Ile Thr Arg Leu Thr Gly Pro Phe Arg Ser Met Pro
        355                 360                 365

Gln Ser Gly Val Leu Arg Lys Gly Leu Thr Ile Lys Tyr Asp Glu Val
    370                 375                 380

Met Lys Gln Asp Gly His Val Trp Val Gly Tyr Asn Thr Asn Ser Gly
385                 390                 395                 400

Lys Arg Val Tyr Leu Pro Val Arg Thr Trp Asn Glu Ser Thr Gly Glu
                405                 410                 415

Leu Gly Pro Leu Trp Gly Thr Ile Lys Gly Ser His His His His
            420                 425                 430

His Gly Gly Ser Lys Asn Lys
            435

<210> SEQ ID NO 110
<211> LENGTH: 438
<212> TYPE: PRT
<213> ORGANISM: Artificial sequence
<220> FEATURE:
<223> OTHER INFORMATION: Fusion protein comprising CHAP domain of LysK
      endolysin, M23 endopeptidase domain of lysostaphin, cell wall
      binding domain of ALE-1, His6-tag and synthetic peptide KNK; incl.
      mutations K17E,H51Q, K28N, T86A and G154S; w/o N-terminal
      methionine

<400> SEQUENCE: 110

Ala Lys Thr Gln Ala Glu Ile Asn Lys Arg Leu Asp Ala Tyr Ala Glu
1               5                   10                  15

Gly Thr Val Asp Ser Pro Tyr Arg Val Lys Asn Ala Thr Ser Tyr Asp
            20                  25                  30

Pro Ser Phe Gly Val Met Glu Ala Gly Ala Ile Asp Ala Asp Gly Tyr
        35                  40                  45

Tyr Gln Ala Gln Cys Gln Asp Leu Ile Thr Asp Tyr Val Leu Trp Leu
    50                  55                  60

Thr Asp Asn Lys Val Arg Thr Trp Gly Asn Ala Lys Asp Gln Ile Lys
65                  70                  75                  80

Gln Ser Tyr Gly Ala Gly Phe Lys Ile His Glu Asn Lys Pro Ser Thr
            85                  90                  95

Val Pro Lys Lys Gly Trp Ile Ala Val Phe Thr Ser Gly Ser Tyr Glu
            100                 105                 110

Gln Trp Gly His Ile Gly Ile Val Tyr Asp Gly Gly Asn Thr Ser Thr
        115                 120                 125

Phe Thr Ile Leu Glu Gln Asn Trp Asn Gly Tyr Ala Asn Lys Lys Pro
    130                 135                 140
```

-continued

```
Thr Lys Arg Val Asp Asn Tyr Tyr Ser Leu Thr His Phe Ile Glu Ile
145                 150                 155                 160

Pro Val Lys Ala Gly Thr Thr Val Lys Lys Glu Thr Ala Lys Lys Ser
            165                 170                 175

Ala Thr Ser His Glu His Ser Ala Gln Trp Leu Asn Asn Tyr Lys Lys
            180                 185                 190

Gly Tyr Gly Tyr Gly Pro Tyr Pro Leu Gly Ile Asn Gly Gly Met His
        195                 200                 205

Tyr Gly Val Asp Phe Phe Met Asn Ile Gly Thr Pro Val Lys Ala Ile
    210                 215                 220

Ser Ser Gly Lys Ile Val Glu Ala Gly Trp Ser Asn Tyr Gly Gly Gly
225                 230                 235                 240

Asn Gln Ile Gly Leu Ile Glu Asn Asp Gly Val His Arg Gln Trp Tyr
                245                 250                 255

Met His Leu Ser Lys Tyr Asn Val Lys Val Gly Asp Tyr Val Lys Ala
                260                 265                 270

Gly Gln Ile Ile Gly Trp Ser Gly Ser Thr Gly Tyr Ser Thr Ala Pro
            275                 280                 285

His Leu His Phe Gln Arg Met Val Asn Ser Phe Ser Asn Ser Thr Ala
        290                 295                 300

Gln Asp Pro Met Pro Phe Leu Lys Ser Ala Gly Tyr Gly Lys Ala Gly
305                 310                 315                 320

Gly Thr Val Thr Pro Thr Pro Asn Pro Gly Asn Gly Tyr Lys Thr Asn
                325                 330                 335

Lys Tyr Gly Thr Leu Tyr Lys Ser Glu Ser Ala Ser Phe Thr Ala Asn
                340                 345                 350

Thr Asp Ile Ile Thr Arg Leu Thr Gly Pro Phe Arg Ser Met Pro Gln
            355                 360                 365

Ser Gly Val Leu Arg Lys Gly Leu Thr Ile Lys Tyr Asp Glu Val Met
370                 375                 380

Lys Gln Asp Gly His Val Trp Val Gly Tyr Asn Thr Asn Ser Gly Lys
385                 390                 395                 400

Arg Val Tyr Leu Pro Val Arg Thr Trp Asn Glu Ser Thr Gly Glu Leu
                405                 410                 415

Gly Pro Leu Trp Gly Thr Ile Lys Gly Ser His His His His His His
            420                 425                 430

Gly Gly Ser Lys Asn Lys
        435
```

```
<210> SEQ ID NO 111
<211> LENGTH: 439
<212> TYPE: PRT
<213> ORGANISM: Artificial sequence
<220> FEATURE:
<223> OTHER INFORMATION: Fusion protein comprising CHAP domain of LysK
      endolysin, M23 endopeptidase domain of lysostaphin, cell wall
      binding domain of ALE-1, His6-tag and synthetic peptide KNK; incl.
      mutations K17E,H51Q, K28N, T86A and G154S

<400> SEQUENCE: 111
```

```
Met Ala Lys Thr Gln Ala Glu Ile Asn Lys Arg Leu Asp Ala Tyr Ala
1               5                   10                  15

Glu Gly Thr Val Asp Ser Pro Tyr Arg Val Lys Asn Ala Thr Ser Tyr
            20                  25                  30

Asp Pro Ser Phe Gly Val Met Glu Ala Gly Ala Ile Asp Ala Asp Gly
        35                  40                  45
```

```
Tyr Tyr Gln Ala Gln Cys Gln Asp Leu Ile Thr Asp Tyr Val Leu Trp
 50                  55                  60
Leu Thr Asp Asn Lys Val Arg Thr Trp Gly Asn Ala Lys Asp Gln Ile
 65                  70                  75                  80
Lys Gln Ser Tyr Gly Ala Gly Phe Lys Ile His Glu Asn Lys Pro Ser
                 85                  90                  95
Thr Val Pro Lys Lys Gly Trp Ile Ala Val Phe Thr Ser Gly Ser Tyr
            100                 105                 110
Glu Gln Trp Gly His Ile Gly Ile Val Tyr Asp Gly Gly Asn Thr Ser
                115                 120                 125
Thr Phe Thr Ile Leu Glu Gln Asn Trp Asn Gly Tyr Ala Asn Lys Lys
    130                 135                 140
Pro Thr Lys Arg Val Asp Asn Tyr Tyr Ser Leu Thr His Phe Ile Glu
145                 150                 155                 160
Ile Pro Val Lys Ala Gly Thr Thr Val Lys Lys Glu Thr Ala Lys Lys
                165                 170                 175
Ser Ala Thr Ser His Glu His Ser Ala Gln Trp Leu Asn Asn Tyr Lys
            180                 185                 190
Lys Gly Tyr Gly Tyr Gly Pro Tyr Pro Leu Gly Ile Asn Gly Gly Met
        195                 200                 205
His Tyr Gly Val Asp Phe Phe Met Asn Ile Gly Thr Pro Val Lys Ala
    210                 215                 220
Ile Ser Ser Gly Lys Ile Val Glu Ala Gly Trp Ser Asn Tyr Gly Gly
225                 230                 235                 240
Gly Asn Gln Ile Gly Leu Ile Glu Asn Asp Gly Val His Arg Gln Trp
                245                 250                 255
Tyr Met His Leu Ser Lys Tyr Asn Val Lys Val Gly Asp Tyr Val Lys
            260                 265                 270
Ala Gly Gln Ile Ile Gly Trp Ser Gly Ser Thr Gly Tyr Ser Thr Ala
        275                 280                 285
Pro His Leu His Phe Gln Arg Met Val Asn Ser Phe Ser Asn Ser Thr
    290                 295                 300
Ala Gln Asp Pro Met Pro Phe Leu Lys Ser Ala Gly Tyr Gly Lys Ala
305                 310                 315                 320
Gly Gly Thr Val Thr Pro Thr Pro Asn Pro Gly Asn Gly Tyr Lys Thr
                325                 330                 335
Asn Lys Tyr Gly Thr Leu Tyr Lys Ser Glu Ser Ala Ser Phe Thr Ala
            340                 345                 350
Asn Thr Asp Ile Ile Thr Arg Leu Thr Gly Pro Phe Arg Ser Met Pro
        355                 360                 365
Gln Ser Gly Val Leu Arg Lys Gly Leu Thr Ile Lys Tyr Asp Glu Val
    370                 375                 380
Met Lys Gln Asp Gly His Val Trp Val Gly Tyr Asn Thr Asn Ser Gly
385                 390                 395                 400
Lys Arg Val Tyr Leu Pro Val Arg Thr Trp Asn Glu Ser Thr Gly Glu
                405                 410                 415
Leu Gly Pro Leu Trp Gly Thr Ile Lys Gly Ser His His His His
            420                 425                 430
His Gly Gly Ser Lys Asn Lys
            435
```

ANTIMICROBIAL AGENTS AGAINST STAPHYLOCOCCUS AUREUS

This application is a national phase application under 35 U.S.C. § 371 of International Application No. PCT/EP2017/079769, filed Nov. 20, 2017, which claims benefit of priority to European Application No. 16199528.7, filed Nov. 18, 2016, the entire contents of each of which are hereby incorporated by reference.

Sequence Listing

The contents of the electronic sequence listing created on May 16, 2019, named DEBEP0147US_ST25.txt and 85,623 bytes in size, is hereby incorporated by reference in its entirety.

The present invention relates to the field of antimicrobial agents active against *Staphylococcus aureus* bacteria. In particular, the present invention relates to polypeptides comprising the CHAP domain of LysK endolysin, the M23 endopeptidase domain of lysostaphin, the cell wall binding domain (CBD) of ALE-1, and a further peptide selected from the group consisting of an antimicrobial peptide, an amphipathic peptide, a cationic peptide, a hydrophobic peptide, a sushi peptide and a defensin. In addition, the present invention relates to nucleic acids encoding such polypeptides, vectors comprising such nucleic acids, and corresponding host cells, compositions and devices. Finally, the present invention relates to applications of the inventive polypeptides, in particular in the pharmaceutical field.

Bacterial pathogens represent a significant threat for human health. Although various types of agents having bactericidal or bacteriostatic activity are known in the art (e.g. antibiotics), microbial resistance to these, in particular to antibiotics, is steadily increasing. One of the pathogens representing a health concern are *Staphylococcus aureus* bacteria. *S. aureus* is one of the most common causes of bacteremia, infective endocarditis, as well as bone and joint infections. Furthermore, it can cause skin and soft tissue infections as well as food poisoning. *S. aureus* rapidly develops resistance to antibiotics, as illustrated by multi-drug resistant (MDR), methicillin-resistant *S. aureus* (MRSA) and the reduced susceptibility to vancomycin (vancomycin-intermediate strains). Since increasing resistance diminishes the utility of conventional antibiotics, there is a constant demand for new antimicrobial agents to control the number of *Staphylococcus aureus*, e.g. in in the nosocomial (hospital) environment.

An agent highly active against *Staphylococcus aureus* bacteria is lysostaphin. Lysostaphin is a peptidoglycan hydrolase which is capable of degrading the cell wall peptidoglycan of *Staphylococcus aureus* bacteria. It is produced by *Staphylococcus simulans* biovar staphylolyticus. Lysostaphin exhibits two domains: a N-terminal catalytic M23 endopeptidase domain and a C-terminal cell wall binding domain (CBD). However, *S. aureus* also rapidly develops resistance against lysostaphin.

Recently, Becker et al. (Sci Rep. 2016 Apr. 28; 6:25063; incorporated herewith by reference) reported the generation of fusion proteins, wherein antimicrobial activities from lysostaphin and LysK endolysin were combined. The resulting fusion protein reduced the incidence of resistant strain development significantly.

However, there is still a constant need for new antibacterial agents active against *Staphylococcus aureus* bacteria. Preferably, said agents show reduced incidence of resistant strain development while exhibiting in parallel a high antibacterial activity, as reflected by a low minimum inhibitory concentration (MIC).

The problem to be solved by the present invention was thus to provide new antibacterial against agents *Staphylococcus aureus* bacteria which show reduced incidence of resistant strain development while exhibiting in parallel a high antibacterial activity.

This object is solved by the subject matter defined in the claims and set forth below.

The term "polypeptide" as used herein refers in particular to a polymer of amino acids linked by peptide bonds in a specific sequence. The amino acid residues of a polypeptide may be modified by e.g. covalent attachments of various groups such as carbohydrates and phosphate. Other substances may be more loosely associated with the polypeptide, such as heme or lipid, giving rise to conjugated polypeptides which are also comprised by the term "polypeptide" as used herein. The term as used herein is intended to encompass also proteins. Thus, the term "polypeptide" also encompasses for example complexes of two or more amino acid polymer chains. The term "polypeptide" does encompass embodiments of polypeptides which exhibit optionally modifications typically used in the art, e.g. biotinylation, acetylation, pegylation, chemical changes of the amino-, SH- or carboxyl-groups (e.g. protecting groups) etc. As will become apparent from the description below, the polypeptide according to the present invention is a non-naturally occurring polypeptide. The term "polypeptide", as used herein, is not limited to a specific length of the amino acid polymer chain, but typically the polypeptide will exhibit a length of more than 250 amino acids. Usually, but not necessarily, a typical polypeptide of the present invention will not exceed about 750 amino acids in length, preferably not exceed about 450 amino acids in length.

The term "variant sequence", as used herein, refers to an amino acid sequence which exhibits, in comparison to the respective reference sequence, one or more additions, deletions, insertions, and/or substitutions and combinations thereof. This includes for example combinations of deletions/insertions, insertions/deletions, deletions/additions, additions/deletions, insertion/additions, additions/insertions etc. A person skilled in the art will however understand that the presence of an amino acid residue at a certain position of the variant sequence which is different from the one that is present at the respective same position in the reference sequence is not a combination of, for example, a deletion and a subsequent insertion at the same position but is a substitution as defined herein. Rather, if reference is made herein to combinations of one or more of additions, deletions, insertions, and substitutions, then combination of changes at distinct positions in the sequence are intended, e.g. an addition at the N-terminus and an intrasequential deletion. Such derived sequence will exhibit a certain level of sequence identity with the respective reference sequence, for example a given SEQ ID NO, which is preferably at least 80%, at least 85%, at least 90%, at least 95%, at least 96%, at least 97%, at least 98% or at least 99%. Preferred variant sequences are fragments of the parent molecule, for example a given SEQ ID NO, retaining the activity of the parent molecule, i.e. exhibiting on a general level same activity as the respective parent molecule. However, said activity can be the same, higher or lower as the respective parent molecule. Also preferred variant sequences are those resulting from conservative amino acid substitutions within the parent sequence, for example a given SEQ ID NO, again retaining the activity of the parent molecule on a general level.

As used herein, the term "% sequence identity", has to be understood as follows: Two sequences to be compared are aligned to give a maximum correlation between the sequences. This may include inserting "gaps" in either one or both sequences, to enhance the degree of alignment. A % identity may then be determined over the whole length of each of the sequences being compared (so-called global alignment), that is particularly suitable for sequences of the same or similar length, or over shorter, defined lengths (so-called local alignment), that is more suitable for sequences of unequal length. In the above context, an amino acid sequence having a "sequence identity" of at least, for example, 95% to a query amino acid sequence, is intended to mean that the sequence of the subject amino acid sequence is identical to the query sequence except that the subject amino acid sequence may include up to five amino acid alterations per each 100 amino acids of the query amino acid sequence. In other words, to obtain an amino acid sequence having a sequence of at least 95% identity to a query amino acid sequence, up to 5% (5 of 100) of the amino acid residues in the subject sequence may be inserted or substituted with another amino acid or deleted. Methods for comparing the identity and homology of two or more sequences are well known in the art. The percentage to which two sequences are identical can for example be determined by using a mathematical algorithm. A preferred, but not limiting, example of a mathematical algorithm which can be used is the algorithm of Karlin et al. (1993), PNAS USA, 90:5873-5877. Such an algorithm is integrated in the BLAST family of programs, e.g. BLAST or NBLAST program (see also Altschul et al., 1990, J. Mol. Biol. 215, 403-410 or Altschul et al. (1997), Nucleic Acids Res, 25:3389-3402), accessible through the home page of the NCBI at world wide web site ncbi.nlm.nih.gov) and FASTA (Pearson (1990), Methods Enzymol. 83, 63-98; Pearson and Lipman (1988), Proc. Natl. Acad. Sci. U.S.A. 85, 2444-2448.). Sequences which are identical to other sequences to a certain extent can be identified by these programmes. Furthermore, programs available in the Wisconsin Sequence Analysis Package, version 9.1 (Devereux et al, 1984, Nucleic Acids Res., 387-395), for example the programs BESTFIT and GAP, may be used to determine the % identity between two polypeptide sequences. BESTFIT uses the "local homology" algorithm of (Smith and Waterman (1981), J. Mol. Biol. 147, 195-197.) and finds the best single region of similarity between two sequences. If herein reference is made to an amino acid sequence sharing a particular extent of sequence identity to a reference sequence, then said difference in sequence is preferably due to conservative amino acid substitutions. Preferably, such sequence retains the activity of the reference sequence, e.g. albeit maybe at a slower rate. In addition, if reference is made herein to a sequence sharing "at least" at certain percentage of sequence identity, then 100% sequence identity are preferably not encompassed.

The term "further peptide", as used herein refers to an amino acid subsequence within the amino acid sequence of the polypeptide of the invention. Said sequence may be the sequence of a cationic peptide, a polycationic peptide, an amphipathic peptide, a hydrophobic peptide, a sushi peptide and/or an antimicrobial peptide. The term does not refer to conventional tags like His-tags, such as His5-tags, His6-tags, His7-tags, His8-tags, His9-tags, His10-tags, His11-tags, His12-tags, His16-tags and His20-tags, Strep-tags, Avi-tags, Myc-tags, Gst-tags, JS-tags, cystein-tags, FLAG-tags or other tags known in the art, thioredoxin or maltose binding proteins (MBP). Preferably, the sequence of the further peptide has a length of at least about 3 to at most about 50, preferably at most about 39 amino acid residues. The further peptide sequence itself does not provide any of the following enzymatic activities: endopeptidase, chitinase, T4 like muraminidase, lambda like muraminidase, N-acetyl-muramoyl-L-alanine-amidase (amidase), muramoyl-L-alanine-amidase, muramidase, lytic transglycosylase (C), lytic transglycosylase (M), N-acetyl-muramidase (lysozyme), N-acetyl-glucosaminidase or transglycosylase. Typically, the further peptide sequence will not provide any enzymatic activity at all.

As used herein, the term "cationic peptide" refers to a peptide having positively charged amino acid residues. Preferably a cationic peptide has a pKa-value of 9.0 or greater. Typically, at least four of the amino acid residues of the cationic peptide can be positively charged, for example, lysine or arginine. "Positively charged" refers to the side chains of the amino acid residues which have a net positive charge at about physiological conditions. The term "cationic peptide" as used herein refers also to polycationic peptides, but also includes cationic peptides which comprise for example less than 20%, preferably less than 10% positively charged amino acid residues.

The term "polycationic peptide" as used herein refers to a peptide composed of mostly positively charged amino acid residues, in particular lysine and/or arginine residues. A peptide is composed of mostly positively charged amino acid residues if at least about 20, 30, 40, 50, 60, 70, 75, 80, 85, 90, 95 or about 100% of the amino acid residues are positively charged amino acid residues, in particular lysine and/or arginine residues. The amino acid residues being not positively charged amino acid residues can be neutrally charged amino acid residues and/or negatively charged amino acid residues and/or hydrophobic amino acid residues. Preferably the amino acid residues being not positively charged amino acid residues are neutrally charged amino acid residues, in particular serine and/or glycine.

The term, "antimicrobial peptide" (AMP) as used herein refers to any naturally occurring peptide that has microbicidal and/or microbistatic activity on, for example, bacteria, viruses, fungi, yeasts, mycoplasma and protozoa. Thus, the term "antimicrobial peptide" as used herein refers in particular to any peptide having anti-bacterial, anti-fungal, anti-mycotic, anti-parasitic, anti-protozoal, anti-viral, anti-infectious, anti-infective and/or germicidal, algicidal, amoebicidal, microbicidal, bactericidal, fungicidal, parasiticidal, protozoacidal, protozoicidal properties. Preferred are anti-bacterial peptides. The antimicrobial peptide may be a member of the RNase A super family, a defensin, cathelicidin, granulysin, histatin, psoriasin, dermicidine or hepcidin. The antimicrobial peptide may be naturally occurring in insects, fish, plants, arachnids, vertebrates or mammals. Preferably the antimicrobial peptide may be naturally occurring in radish, silk moth, wolf spider, frog, preferably in *Xenopus laevis, Rana* frogs, more preferably in *Rana catesbeiana*, toad, preferably Asian toad *Bufo bufo gargarizans*, fly, preferably in *Drosophila*, more preferably in *Drosophila melanogaster*, in *Aedes aegypti*, in honey bee, bumblebee, preferably in *Bombus pascuorum*, flesh fly, preferably in *Sarcophaga peregrine*, scorpion, horseshoe crab, catfish, preferably in *Parasilurus asotus*, cow, pig, sheep, porcine, bovine, monkey and human. As used herein, an "antimicrobial peptide" (AMP) may in particular be a peptide which is not a cationic peptide, polycationic peptide, amphipathic peptide, sushi peptide, defensins, and hydrophobic peptide, but nevertheless exhibits antimicrobial activity.

The term "sushi peptide" as used herein refers to complement control proteins (CCP) having short consensus repeats. The sushi module of sushi peptides functions as a protein-protein interaction domain in many different proteins. Peptides containing a Sushi domain have been shown to have antimicrobial activities. Preferably, sushi peptides are naturally occurring peptides.

The term "defensin" as used herein refers to a peptide present within animals, preferably mammals, more preferably humans, wherein the defensin plays a role in the innate host defence system as the destruction of foreign substances such as infectious bacteria and/or infectious viruses and/or fungi. A defensin is a non-antibody microbicidal and/or tumoricidal protein, peptide or polypeptide. Examples for "defensins" are "mammalian defensins," alpha-defensins, beta-defensins, indolicidin and magainins. The term "defensins" as used herein refers both to an isolated form from animal cells or to a synthetically produced form, and refers also to variants which substantially retain the cytotoxic activities of their parent proteins, but whose sequences have been altered by insertion or deletion of one or more amino acid residues.

The term "amphipathic peptide" as used herein refers to peptides having both hydrophilic and hydrophobic functional groups. Preferably, the term "amphipathic peptide" as used herein refers to a peptide having a defined arrangement of hydrophilic and hydrophobic groups e.g. amphipathic peptides may be e.g. alpha helical, having predominantly non polar side chains along one side of the helix and polar residues along the rest of its surface.

The term "hydrophobic group" as used herein refers preferably to chemical groups such as amino acid side chains which are substantially water insoluble, but soluble in an oil phase, with the solubility in the oil phase being higher than that in water or in an aqueous phase. In water, amino acid residues having a hydrophobic side chain interact with one another to generate a non-aqueous environment. Examples of amino acid residues with hydrophobic side chains are valine, isoleucine, leucine, methionine, phenylalanine, tryptophan, cysteine, alanine, tyrosine, and proline residues The term "hydrophobic peptide" as used herein refers to a hydrophobic peptide, which is preferably composed of mostly amino acid residues with hydrophobic groups. Such peptide is preferably composed of mostly hydrophobic amino acid residues, i.e. at least about 20, 30, 40, 50, 60, 70, 75, 80, 85, 90, 95 or at least about 100% of the amino acid residues are hydrophobic amino acid residues. The amino acid residues being not hydrophobic are preferably neutral and preferably not hydrophilic.

As used herein, the term "tag" refers to an amino acid sequence, which is typically in the art fused to or included in another amino acid sequence for a) improving expression of the overall amino acid sequence or polypeptide, b) facilitating purification of the overall amino acid sequence or polypeptide, c) facilitating immobilisation of the overall amino acid sequence or polypeptide, and/or d) facilitating detection of the overall amino acid sequence or polypeptide. Examples for tags are His tags, such as His5-tags, His6-tags, His7-tags, His8-tags, His9-tags, His10-tags, His11-tags, His12-tags, His16-tags and His20-tags, Strep-tags, Avi-tags, Myc-tags, GST-tags, JS-tags, cystein-tags, FLAG-tags, HA-tags, thioredoxin or maltose binding proteins (MBP), CAT, GFP, YFP, etc. The person skilled in the art will know a vast number of tags suitable for different technical applications.

The tag may for example make such tagged polypeptide suitable for e.g. antibody binding in different ELISA assay formats or other technical applications.

The term "comprising" as used herein shall not be construed as being limited to the meaning "consisting of" (i.e. excluding the presence of additional other matter). Rather, "comprising" implies that optionally additional matter may be present. The term "comprising" encompasses as particularly envisioned embodiments falling within its scope "consisting of" (i.e. excluding the presence of additional other matter) and "comprising but not consisting of" (i.e. requiring the presence of additional other matter), with the former being more preferred.

The inventors of the present invention have surprisingly found new polypeptide agents which exhibit a high antibacterial activity and in parallel a reduced incidence of resistant strain development. In both aspects the polypeptides of the present invention represent an improvement over the best fusion protein of Becker et al. (Sci Rep. 2016 Apr. 28; 6:25063), the L-K construct.

Therefore, the present invention relates in a first aspect to a polypeptide comprising:
 i) the CHAP domain of LysK endolysin (or a variant sequence thereof exhibiting at least 80% sequence identity with the CHAP domain of LysK endolysin);
 ii) the M23 endopeptidase domain of lysostaphin (or a variant sequence thereof exhibiting at least 80% sequence identity with the M23 endopeptidase domain of lysostaphin);
 iii) the cell wall binding domain (CBD) of ALE-1 (or a variant thereof exhibiting at least 90% sequence identity with the cell wall binding domain (CBD) of ALE-1), and
 iv) a further peptide selected from the group consisting of an antimicrobial peptide, an amphipathic peptide, a cationic peptide, a hydrophobic peptide, a sushi peptide and a defensin.

The inventive polypeptide comprises at least four sequence elements. The first element is the CHAP domain (cysteine-histidine dependent amido-hydrolase/peptidase domain) of LysK endolysin (see SEQ ID NO:1) or a variant sequence thereof. The polypeptide of the invention may comprise aside of the CHAP domain of LysK also corresponding longer sequence elements of LysK and respective variant sequences. For example, the polypeptide may comprise the sequence of SEQ ID NO:2, which reflects the N-terminal part of LysK endolysin (including the CHAP domain) but for the N-terminal methionine. The second element is the M23 endopeptidase domain of lysostaphin (see SEQ ID NO:3) or a variant sequence thereof. This domain is the catalytic domain of the bacteriocin lysostaphin. The polypeptide of the invention may comprise aside of the M23 endopeptidase domain of lysostaphin also longer sequence elements (and respective variant sequences), such as the sequence of SEQ ID NO:4, which reflects the N-terminal part of lysostaphin (aa 4-152; including the M23 endopeptidase domain). The third element is the cell wall binding domain (CBD) of ALE-1 endolysin (see SEQ ID NO:5) or a variant sequence thereof. This is a non-catalytic domain. The polypeptide of the invention may comprise aside of the CBD of ALE-1 endolysin also longer sequence elements of ALE-1 endolysin (and respective variant sequences), such as the sequence of SEQ ID NO:6, which reflects the C-terminal part of ALE-1 endolysin (aa 234-327; including the CBD domain). The two catalytic domains (CHAP, M23) and the CBD domain (of ALE-1) may in principle occur in any order. However, preferably the different elements (irrespective whether they are the natural occurring or variant sequences) are arranged as follows (from N- to C-terminus): CHAP domain—M23-endopeptidase—CBD of ALE-1. There may also be other, e.g. intervening, sequence elements present. Preferably, the intervening sequences are short linker sequences not exceeding in each case more than 10, more preferably not more than 5 amino acids in length. Most preferably, they are only one or two amino acids in length. Linker sequences are preferably flexible sequences, comprising one or more glycine residues. An example for such linker is a glycine-serine linker or the sequence GGGGS (SEQ ID NO: 7). Preferably, the fourth element of the inventive polypeptide, the further peptide (see below) is positioned N- or C-terminal of the unit formed by the two catalytic domains (CHAP, M23) and the CBD domain (of ALE-1), with the C-terminal position being more preferred. If the the two catalytic domains (CHAP, M23) and the CBD domain form a unit (i.e. the peptide is C- or N-terminal of said unit), then said unit is preferably less than 500 amino acids in length, preferably less than 450 amino acids in length. It is preferred if a polypeptide according to the first aspect of the invention comprises at least the amino acid sequence of SEQ ID NO:3 (M23), and/or of SEQ ID NO:5 (ALE-1). Most preferably, the polypeptide according to the present invention comprises in any event the amino acid sequence according to SEQ ID NO:5. A preferred arrangement of these last two elements (M23, ALE-1) is reflected in SEQ ID NO:8.

Regarding the CHAP domain the present invention provides a number of possible variant sequence, i.e. there is absolutely no obligation to specifically use the amino acid sequence of SEQ ID NO: 1 or SEQ ID NO:2. Possible mutations (identified vis-a-vis SEQ ID NO:2) are for example K17E, K28N, H51Q, T86A, G153S or G153C, E171G, T172N, or A173R. Most preferred are variant sequences of SEQ ID NO:2, which comprise the mutations K17E and H51Q. Most preferably, said variant sequences comprise the mutations K17E, K28N, H51Q, T86A and G153S. These mutations have been shown to improve antibacterial activity of the polypeptides according to the present invention and to increase thermal stability. If the naturally occurring sequence of SEQ ID NO:2 is employed, then a preferred arrangement of the first three elements of the present invention is reflected in SEQ ID NO:9 (w/o N-terminal methionine) and in SEQ ID NO:10. Contemplated for use in the present invention are also variant sequences thereof, e.g., variant sequences comprising at least 80% sequence identity with SEQ ID NO:8, SEQ ID NO:9 or SEQ ID NO: 10.

The inventive polypeptide comprises—aside of the first three elements (CHAP domain—M23-endopeptidase—CBD of ALE-1)—a fourth element, namely a peptide selected from the group consisting of an antimicrobial peptide, an amphipathic peptide, a cationic peptide, a hydrophobic peptide, a sushi peptide and a defensin. Preferably, the further peptide sequence is heterologous to the CHAP domain of LysK endolysin, the M23 endopeptidase domain of lysostaphin and the cell wall binding domain (CBD) of ALE-1, i.e. the further peptide sequence does not occur in the LysK endolysin sequence, the lysostaphin sequence and/or the ALE-1 endolysin sequence. Preferably, the fourth element of the inventive polypeptide is positioned N- or C-terminal of the unit formed by the two catalytic domains (CHAP, M23) and the CBD domain (of ALE-1), with the C-terminal position being more preferred. Suitable arrangements are thus: a) CHAP domain—M23-endopeptidase—CBD of ALE-1—peptide, and b) Peptide—CHAP domain—M23-endopeptidase—CBD of ALE-1. The peptide may be linked to the enzyme unit (CHAP domain—M23-endopeptidase—CBD of ALE-1) directly or via intervening sequences, e.g. linker sequences.

Examples for cationic/polycationic amino acid sequences, which may be used as further peptide, are listed in the following table.

TABLE 1

| Amino acid sequence | Length | SEQ ID NO: |
|---|---|---|
| KRKKRK | 6 | 11 |
| KRXKR | 5 | 12 |
| KRSKR | 5 | 13 |
| KRGSG | 5 | 14 |
| KRKKRKKRK | 9 | 15 |
| RRRRRRRRR | 9 | 16 |
| KKKKKKKK | 8 | 17 |
| KRKKRKKRKK | 10 | 18 |
| KRKKRKKRKKRK | 12 | 19 |
| KRKKRKRKKRKKR | 14 | 20 |
| KKKKKKKKKKKKKKKK | 16 | 21 |
| KRKKRKRKKRKKRKKRK | 18 | 22 |
| KRKKRKRKKRKRKKRKKK | 19 | 23 |
| RRRRRRRRRRRRRRRRRRR | 19 | 24 |
| KKKKKKKKKKKKKKKKKKK | 19 | 25 |
| KRKKRKRKRSKRKKKRKKRK | 20 | 26 |
| KRKKRKRKRSKRKKRKRKKK | 21 | 27 |
| KRKKRKRKKRKKRKKRKRKR | 21 | 28 |
| KRKKRKKRKRGSGKRKKRKKRK | 22 | 29 |
| KRKKRKKRKRGSGSGKRKKRKKRK | 24 | 30 |
| KRKKRKKRKKRKRKKRKRKKRKRKK | 25 | 31 |
| KRKKRKKRKRSKRKKRKKRKRKSKRKRKKKRK | 31 | 32 |
| KRKKRKKRKRGSGSGKRKKRKKRKGSGSGKRKKRKKKRK | 38 | 33 |
| KRKKRKKRKKRKRKKRKRKKRKRKKRKRKKRKRKKRKKR | 39 | 34 |
| KRKKRKKRKRSKRKKRKKRKRKSKRKRKKKRKRSKRKKRKKRK | 42 | 35 |
| KNA | 3 | 36 |
| GGSKNA | 6 | 37 |
| KNK | 3 | 38 |
| GGSKNK | 6 | 39 |

Examples for antimicrobial amino acid sequences which may be used in carrying out the present invention are listed in the following table.

TABLE 2

| Peptide | Sequence | SEQ ID NO |
|---|---|---|
| LL-37 | LLGDFFRKSKEKIGKEFKRIVQRIKDFLRNLVPRTES | 40 |
| SMAP-29 | RGLRRLGRKIAHGVKKYGPTVLRIIRIAG | 41 |
| Indolicidin | ILPWKWPWWPWRR | 42 |
| Protegrin | RGGRLCYCRRRFCVCVGR | 43 |
| Cecropin P1 | SWLSKTAKKLENSAKKRISEGIAIAIQGGPR | 44 |
| Magainin | GIGKFLHSAKKFGKAFVGEIMNS | 45 |
| Pleurocidin | GWGSFFKKAAHVGKHVGKAALTHYL | 46 |
| Cecropin A (A. aegypti) | GGLKKLGKKLEGAGKRVFNAAEKALPVVAGAKALRK | 47 |
| Cecropin A (D. melanogaster) | GWLKKIGKKIERVGQHTRDATIQGLGIPQQAANVAATARG | 48 |
| Buforin II | TRSSRAGLQFPVGRVHRLLRK | 49 |
| Sarcotoxin IA | GWLKKIGKKIERVGQHTRDATIQGLGIAQQAANVAATAR | 50 |
| Apidaecin | ANRPVYIPPPRPPHPRL | 51 |
| Ascaphine 5 | GIKDWIKGAAKKLIKTVASHIANQ | 52 |
| Nigrocine 2 | GLLSKVLGVGKKVLCGVSGLVC | 53 |
| Pseudin 1 | GLNTLKKVFQGLHEAIKLINNHVQ | 54 |
| Ranalexin | FLGGLIVPAMICAVTKKC | 55 |
| Melittin | GIGAVLKVLTTGLPALISWIKRKRQQ | 56 |
| Lycotoxin 1 | IWLTALKFLGKHAAKKLAKQQLSKL | 57 |
| Parasin 1 | KGRGKQGGKVRAKAKTRSS | 58 |
| Buforin I | AGRGKQGGKVRAKAKTRSSRAGLQFPVGRVHRLLRKGNY | 59 |
| Dermaseptin 1 | ALWKTMLKKLGTMALHAGKAALGAAADTISQGTQ | 60 |
| Bactenecin 1 | RLCRIVVIRVCR | 61 |
| Thanatin | GSKKPVPIIYCNRRTGKCQRM | 62 |
| Brevinin 1T | VNPIILGVLPKVCLITKKC | 63 |
| Ranateurin 1 | SMLSVLKNLGKVGLGFVACKINIKQC | 64 |
| Esculentin 1 | GIFSKLGRKKIKNLLISGLKNVGKEVGMDVVRTGIKIAGCKIKGEC | 65 |
| Tachyplesin | RWCFRVCYRGICYRKCR | 66 |
| Androctonin | RSVCRQIKICRRGGCYYKCTNRPY | 67 |
| alpha-defensin | DCYCRIPACIAGERRYGTCIYQGRLWAFCC | 68 |
| beta-defensin | NPVSCVRNKGICVPIRCPGSMKQIGTCVGRAVKCCRKK | 69 |
| theta-defensin | GFCRCLCRRGVCRCICTR | 70 |
| defensin (sapecin A) | ATCDLLSGTGINHSACAAHCLLRGNRGGYCNGKAVCVCRN | 71 |
| Thionin (crambin) | TTCCPSIVARSNFNVCRIPGTPEAICATYTGCIIIPGATCPGDYAN | 72 |

TABLE 2-continued

| Peptide | Sequence | SEQ ID NO |
|---|---|---|
| defensin from radish | QKLCQRPSGTWSGVCGNNNACKNQCIRLEKARHG SCNYVFPAHCICYFPC | 73 |
| Drosomycin | DCLSGRYKGPCAVWDNETCRRVCKEEGRSSGHCS PSLKCWCEGC | 74 |
| Hepcidin | DTHFPICIFCCGCCHRSKCGMCCKT | 75 |
| Bac 5 | RFRPPIRRPPIRPPFYPPFRPPIRPPIFPPIRPP FRPPLGRPFP | 76 |
| PR-39 | RRRPRPPYLPRPRPPPFFPPRLPPRIPPGFPPRF PPRFP | 77 |
| Pyrrhocoricin | VDKGSYLPRPTPPRPIYNRN | 78 |
| Histatin 5 | DSKAKRHHGYKRKFHEKHHSHRGY | 79 |
| ECP19 | RPPQFTRAQWFAIQHISLN | 80 |
| MSI-594 | GIGKFLKKAKKGIGAVLKVLTTG | 81 |
| TL-ColM | METLTVHAPSPSTNLPSYGNGAFSLSAPHVPGAG P | 82 |
| SBO | KLKKIAQKIKNFFAKLVA | 83 |
| Macedocin | GKNGVFKTISHECHLNTWAFLATCCS | 84 |
| Macedocin (Trunc) | GKNGVFKTISHECHLNTWAFLA | 85 |
| D16 | ACKLKSLLKTLSKAKKKKLKTLLKALSK | 86 |
| CPF-C1 | GFGSLLGKALRLGANVL | 87 |
| TL-ColM(-Met) | ETLTVHAPSPSTNLPSYGNGAFSLSAPHVPGAGP | 88 |
| TM-174E | LISKGWPYLLVVVLGATIYFWGNSNG | 89 |
| ECP45 | RPPQFTRAQWFAIQHISLNPPRCTIAMRAINNYR WRCKNQNTFLR | 90 |
| ColicinE3_1-51 (S37F) | SGGDGRGHNTGAHSTSGNINGGPTGLGVGGGASD GFGWSSENNPWGGGSG | 91 |
| ColicinE3_1-69 (S37F) | SGGDGRGHNTGAHSTSGNINGGPTGLGVGGGASD GFGWSSENNPWGGGSGSGIHWGGGSGHGNGGGNG | 92 |
| ColicinD_1-53 | SDYEGSGPTEGIDYGHSMVVWPSTGLISGGDVKP GGSSGIAPSMPPGWGDYS | 93 |
| Cathepsin G (77-83) | HPQYNQR | 94 |

The further may be a sushi peptide which is described by Ding J L, Li P, Ho B Cell Mol Life Sci. 2008 April; 65(7-8):1202-19. The Sushi peptides: structural characterization and mode of action against Gram-negative bacteria. Especially preferred is the sushi 1 peptide according to SEQ ID NO: 95. Other preferred sushi peptides are sushi peptides 51 and S3 and multiples thereof (Tan et al, FASEB J. 2000 September; 14(12):1801-13).

Preferred hydrophobic peptides are Walmagh 1 having the amino acid sequence according to SEQ ID NO: 96 and the hydrophobic peptide having the amino acid sequence Phe-Phe-Val-Ala-Pro (SEQ ID NO: 97).

Preferred amphipathic peptides are α4-helix of T4 lysozyme according to SEQ ID NO: 98 and WLBU2-Variant having the amino acid sequence according to SEQ ID NO: 99 and Walmagh 2 according to SEQ ID NO: 100.

More preferably, the sequence of the further peptide is selected from the group consisting of SEQ ID NO: 36, SEQ ID NO: 37, SEQ ID NO: 38, SEQ ID NO: 39 and SEQ ID NO: 94.

Most preferably, the sequence of the further peptide is selected from the group consisting of SEQ ID NO: 38 and SEQ ID NO: 94.

In particular in cases where the inventive polypeptide is to be recombinantly expressed by a host cell, it is preferred if the inventive polypeptide comprises a methionine residue at the N-terminus.

The inventive polypeptide may comprise additionally one or more tag sequences. Such tag sequence may for example be located at the N- or C-terminus of the inventive polypeptide, or between the peptide sequence and the enzyme unit (CHAP domain—M23-endopeptidase—CBD of ALE-1). In a preferred embodiment, the one or more tag sequence is located on the C-terminal side of the enzyme unit (CHAP domain—M23-endopeptidase—CBD of ALE-1). The one or more tag sequences may be linked for example directly or via a short linker to the enzyme unit (see above). Numerous examples for tags are known in the art, some of which have already been mentioned above. In the context of the present invention a particularly preferred tag sequence is a His-tag, preferably a His tag according to SEQ ID NO: 101. Preferred sequences comprising the enzyme unit (CHAP domain—M23-endopeptidase—CBD of ALE-1) and a tag are SEQ ID NO: 102 and SEQ ID NO: 103 (both with an optional methionine at the N-terminus). The peptide sequence is preferably located C-terminal (e.g. of SEQ ID NO: 102 or SEQ ID NO: 103), either directly linked thereto or via linker sequences.

Particularly preferred examples of polypeptides according to the present invention are polypeptides comprising the sequence of SEQ ID NO:104 (SEQ ID NO:105 with N-terminal methionine) or SEQ ID NO: 106 (SEQ ID NO: 107 with N-terminal methionine). Other examples are SEQ ID NO: 108 (SEQ ID NO:109 with N-terminal methionine) and SEQ ID NO: 110 (SEQ ID NO:111 with N-terminal methionine). The present invention also contemplates to utilize polypeptides comprising variant sequences of any of these eight sequences, in particular variant sequences exhibiting at least 80%, at least 85%, at least 90%, at least 95%, at least 96%, at least 97%, at least 98% or at least 99% sequence identity to any one of these eight sequences. Preferably, said polypeptides are more heat stable and/or exhibit higher activity than the respective reference sequence. Preferably, said variant sequences still comprise the sequence of SEQ ID NO: 38 or SEQ ID NO: 94, and/or still comprise the sequence of SEQ ID NO:5 or SEQ ID NO:6. Sites for variation are in particular those for which the present invention identified suitable mutations. The variant sequences may also lack the N-terminal methionine.

In further aspects the present invention relates to polypeptides comprising an improved CHAP domain of LysK. The inventors have identified mutations which improve the antibacterial activity and/or the thermal stability. As protein domains are capable of folding independently of other domains, these properties will be retained and can be exploited when shuffling this domain with other domains, e.g. of other endolysins.

Therefore, the present invention relates in a second aspect of the present invention to a further polypeptide, said polypeptide comprising a variant sequence of SEQ ID NO:1, wherein said variant sequence comprises at least 80% sequence identity with the amino acid sequence of SEQ ID NO:1, and wherein said variant sequence exhibits mutation H8N and/or T43A compared to the amino acid sequence of SEQ ID NO:1. As said polypeptide needs to exhibit at least one of these two mutations, said polypeptide does not comprises 100% sequence identity with the amino acid sequence of SEQ ID NO:1. Preferably, the polypeptide of the second aspect of the invention exhibits at least the H8N mutation and exhibits most preferably both mutations.

In a third the present invention relates to a further polypeptide comprising a variant sequence of SEQ ID NO:2, wherein said variant sequence comprises at least 80% sequence identity with the amino acid sequence of SEQ ID NO:2, and wherein said variant sequence exhibits one or more mutations selected from the group consisting of K16E, K27N, H50Q, T85A, G153C, O154S compared to the amino acid sequence of SEQ ID NO:2. Preferably, the polypeptide according to the third aspect of the invention comprises a variant sequence exhibiting at least mutations K16E and H50Q compared to the amino acid sequence of SEQ ID NO:2. Even more preferably, the polypeptide according to the third aspect of the invention comprises a variant sequence exhibiting at least mutations K16E, K27N, H50Q, T85A, and G153C compared to the amino acid sequence of SEQ ID NO:2.

The polypeptide of the second or third aspect of the invention may comprise further sequence elements, in particular further domains, such as domains providing the fusion protein with antibacterial activity (for instance against Staphylococci, such as S. aureus). For example, a polypeptide of the second or third aspect of the invention may comprise at least one (e.g. one, two, or more than two) catalytic domains of a peptidoglycan hydrolyse. If the polypeptide of the second or third aspect of the invention comprises more than one additional domain, then said domains may derive from different sources, i.e. may be heterologous to each other.

An example for a polypeptide according to the second or third aspect of the invention may be a polypeptide wherein said variant sequence exhibits at least 95% sequence identity with the amino acid sequence of SEQ ID NO:105, SEQ ID NO: 107, SEQ ID NO:109, or SEQ ID NO:111, preferably at least 96%, at least 97%, at least 98% or at least 99% sequence identity with the amino acid sequence of SEQ ID NO:105, SEQ ID NO: 107, SEQ ID NO:109, or SEQ ID NO:111.

The length of a polypeptide according to any aspect of the present invention is in principle not limited, but preferably the length will not be excessively large. Preferably, a polypeptide according to the present invention has an overall length not exceeding about 600 amino acids, preferably not exceeding about 500 amino acids.

A polypeptide according to the present invention is preferably characterized by the ability to degrade the peptidoglycan of S. aureus bacteria. If the enzyme is active, degradation of the peptidoglycan layer will lead to a drop of turbidity, which can be measured photometrically (see for example Briers et al., J. Biochem. Biophys Methods 70: 531-533, (2007).

The present invention does also relate to nucleic acids encoding one or more inventive polypeptides of the present invention. The inventive nucleic acid may take all forms conceivable for a nucleic acid. In particular the nucleic acids according to the present invention may be RNA, DNA or hybrids thereof. They may be single-stranded or double-stranded. The may have the size of small transcripts or of entire genomes, such as a bacteriophage genome. As used herein, a nucleic acid encoding one or more inventive polypeptides of the present invention may be a nucleic acid reflecting the sense strand. Likewise, the antisense strand is also encompassed. The nucleic acid may encompass a heterologous promotor for expression of the inventive polypeptide.

In a further aspect, the present invention relates to a vector, which comprises a nucleic acid according to the present invention. Such vector may for example be an expression vector allowing for expression of an inventive polypeptide. Said expression may be constitutive or inducible. The vector may also be a cloning vector comprising the nucleic acid sequence of an inventive polypeptide for cloning purposes.

In a further aspect, the present invention relates to a host cell comprising a polypeptide according to the present invention, a nucleic acid according to the present invention, and/or a vector according to the present invention. The host cells may be selected in particular from the group consisting of bacterial cells and yeast cells. Particularly preferred host cells are *E. coli* cells.

In a further aspect, the present invention relates to composition comprising a polypeptide according to the present invention, a nucleic acid according to the present invention, a vector according to the present invention, and/or a host cell according to the present invention and further a suitable diluent, excipient or carrier. Preferred compositions comprise the polypeptide according to the present invention. Preferably, a composition according to the present invention comprises a pharmaceutically acceptable diluent, excipient or carrier. Such composition may be a pharmaceutical composition. Furthermore, a composition according to the present invention, comprising a polypeptide according to the present invention, a nucleic acid according to the present invention, a vector according to the present invention, and/or a host cell according to the present invention, may be an aqueous solution (preferably a buffer or a physiological solution), a powder, a suppository, an emulsion, a suspension, a gel, a lotion, a cream, salve, ointment, injectable solution, syrup, spray, inhalant or any other medical reasonable galenic composition or formulation, a coating composition, preferably an implant coating composition, a stent coating composition, or a catheter coating composition, a biomaterial, preferably bone cement.

In a further aspect the present invention relates to a device, in particular a medical device comprising a polypeptide according to the present invention, a nucleic acid according to the present invention, a vector according to the present invention, a host cell according to the present invention, and/or a composition according the present invention. Such device (or at least a portion thereof) may for example be coated or impregnated with a polypeptide according to the present invention, a nucleic acid according to the present invention, a vector according to the present invention, a host cell according to the present invention, and/or a composition according the present invention. Particularly preferred are coating or impregnation with a polypeptide according to the present invention or a composition according the present invention. Such device may for example be an implant, stent or catheter. These devices may find for example application in cardiac or orthopedic surgery. Other suitable devices of the invention may be plasters, compresses or dressings comprising a polypeptide according to the present invention (or a nucleic acid according to the present invention, a vector according to the present invention, a host cell according to the present invention, and/or a composition according the present invention). These may find for instance application in wound care.

In a further aspect the present invention relates to a polypeptide according to the present invention, a nucleic acid according to the present invention, a vector according to the present invention, a host cell according to the present invention, and/or a composition according the present invention for use in a method for treatment of the human or animal body by surgery or therapy or in diagnostic methods practiced on the human or animal body.

Diagnostic methods practiced on the human or animal body may involve the taking of samples from a subject, establishing bacterial cultures and the analysis whether addition of, e.g., a polypeptide of the present invention to the culture inhibits bacterial growth. If so, presence of *S. aureus* is likely.

If the nucleic acids of the invention or the vector of the present invention is used in this context, then preferably said nucleic acid or vector provides for secretion of an inventive polypeptide from a cell. If a host cell of the invention is used, then it is preferred that the respective host cell secretes an inventive polypeptide.

The present invention also relates to a polypeptide according to the present invention (and likewise a nucleic acid according to the present invention, a vector according to the present invention, a host cell according to the present invention, and/or a composition according to the present invention) for use in a method of treatment or prevention of infections, in particular for use in a method of treatment or prevention of infections involving *S. aureus* bacteria. In this respect the present invention relates also to a polypeptide according to the present invention (and likewise a nucleic acid according to the present invention, a vector according to the present invention, a host cell according to the present invention, and/or a composition according to the present invention) for use in a method of treatment, amelioration or prevention of dermatitis (such as atopic dermatitis) or otitis. *S. aureus* bacteria are frequently involved in these disease states, e.g. as secondary infection.

The present invention also relates to a polypeptide according to the present invention (and likewise a nucleic acid according to the present invention, a vector according to the present invention, a host cell according to the present invention, and/or a composition according to the present invention) for use in a method of treatment of wounds of a subject, in particular acute wounds such as iatrogenic wounds, or chronic wounds. The subject may be, for example, an animal or a human being.

The present invention also relates to a method of treatment or prevention of infections caused by *S. aureus* bacteria in a subject, the method comprising contacting said subject with a polypeptide according to the present invention (or likewise a nucleic acid according to the present invention, a vector according to the present invention, a host cell according to the present invention, and/or a composition according to the present invention). In particular, the present invention relates to a method of treatment or prevention of infections involving *S. aureus* bacteria in a subject, the method comprising contacting said subject with a polypeptide according to the present invention.

In a further aspect the present invention relates to the use of a polypeptide according to the present invention (or a nucleic acid according the present invention, a vector according to the present invention, a host cell according to the present invention, and/or a composition according to the present invention) for disinfecting inanimate surfaces, compositions and/or objects, in particular in the nosocomial environment or in a doctor's office.

In a further aspect, the present invention relates to the use of a polypeptide according to the present invention (or a nucleic acid according the present invention, a vector according to the present invention, a host cell according to the present invention, and/or a composition according to the present invention) for preventing contamination of inanimate surfaces, compositions and/or objects with bacteria, in particular for preventing contamination with *S. aureus* bacteria.

In a further aspect, the present invention relates to a method for disinfecting inanimate surfaces, compositions and/or objects, in particular in the nosocomial environment or in a doctor's office, wherein the method comprises contacting the inanimate surfaces, compositions and/or objects with a polypeptide according to the present invention (or a nucleic acid according the present invention, a vector according to the present invention, a host cell according to the present invention, and/or a composition according to the present invention).

In a further aspect, the present invention relates to a method for preventing contamination of inanimate surfaces, compositions and/or objects with bacteria, in particular for preventing contamination with *S. aureus* bacteria, wherein the method comprises contacting the inanimate surfaces, compositions and/or objects with a polypeptide according to the present invention (or a nucleic acid according the present invention, a vector according to the present invention, a host cell according to the present invention, and/or a composition according to the present invention).

EXAMPLES

In the following a specific example illustrating embodiments and aspects of the invention is presented. However, the present invention shall not to be limited in scope by the specific embodiments described herein. Indeed, various modifications of the invention in addition to those described herein will become readily apparent to those skilled in the art from the foregoing description and the examples below. All such modifications fall within the scope of the appended claims.

Example 1: Antibacterial Activity on *S. aureus* of Two Fusion Proteins of the Invention Becker et al. (Sci Rep. 2016 Apr. 28; 6:25063) reported construction of fusion protein L-K with reduced incidence of resistant *S. aureus* strain development. In an attempt to provide other improved fusion proteins against *S. aureus*, the inventors generated two fusion proteins, each comprising the CHAP domain of LysK endolysin, the M23 endopeptidase domain of lysostaphin; and the cell wall binding domain (CBD) of ALE-1. In addition, one of the fusion proteins did comprise the cathepsin G (77-83) peptide (SEQ ID NO:94), the other the cationic peptide KNK (SEQ ID NO:38). The resulting fusion proteins (SEQ ID NO:105 and SEQ ID NO: 107) were assayed for antibacterial activity and resistance development. For this purpose MIC (minimal inhibitory concentration) assays (see below) were carried out for several culture cycles.

MIC assay *S. aureus* Sp10 was grown in (Luria-Bertani) medium and diluted 1:10 in Mueller-Hinton medium. At an optical density $OD_{600}$ of about 0.6, bacteria were diluted in the same medium 1:10 followed by a 1:500 dilution. Protein buffer (20 mM HEPES, 500 mM NaCl, pH 7.4) and proteins or gentamycin were pipetted into a 96 well plate, using different concentrations of proteins/gentamycin and an end volume of 20 µl. The proteins used were the fusion proteins according to SEQ ID NO:105 and SEQ ID NO: 107. 180 µl of bacterial cells or a medium (Mueller-Hinton) control were given to the 96 well plate and mixed. The plate was incubated for 18-22 hours at 37° C. and the bacterial growth was determined measuring the $OD_{600}$ values of the wells. The well with the lowest concentration of protein/gentamycin showing the same $OD_{600}$ value as the medium control was taken as MIC. For the next cycle, the bacterial solution from the sub-MIC well was used. The sub-MIC well is the well in which the next lower concentration to the MIC concentration was tested, i.e. the well with the highest concentration of protein/gentamycin but still $OD_{600}$ above the medium control. For further cycles of the resistance assay, the bacteria from this sub-MIC well of the previous cycle were taken for the next over-night culture.

The results are given in tables 3a and b below.

TABLE 3a

| | Minimal inhibitory concentration (MIC; µg/ml) | | |
|---|---|---|---|
| Cycle | SEQ ID NO: 105 | SEQ ID NO: 107 | Gentamycin |
| 1 | 4 | 4 | 0.8 |
| 6 | 4 | 4 | 4 |
| 12 | 6 | 6 | 6 |

Table 3b below illustrates said results of table 3a as fold change over the initial MIC (cycle 1).

TABLE 3b

| | Fold change of MIC | | |
|---|---|---|---|
| Cycle | SEQ ID NO: 105 | SEQ ID NO: 107 | Gentamycin |
| 1 | 1 | 1 | 1 |
| 6 | 1 | 1 | 5 |
| 12 | 1.5 | 1.5 | 7.5 |

As evident from table 3b above, both fusion proteins of the invention are less prone to resistant strain development over time than gentamycin.

Moreover, both fusion proteins of the invention showed in comparison to the results reported for the fusion protein L-K of the prior art (see Becker et al. (Sci Rep. 2016 Apr. 28; 6:25063) surprisingly reduced incidence of resistant strain development after more cycles (1.5 fold change MIC for both fusions proteins of the present invention after 12 cycles vs. 2 fold change MIC for L-K fusion protein of Becker et al. after 10 cycles (see Becker et al. FIG. 1B), while exhibiting in parallel a higher antibacterial activity (initial MIC of 4 µg/ml for the fusion proteins of the present invention vs. 7.8 µg/ml for the L-K fusion protein of Becker et al.).

Example 2: Variants of Polypeptides According to the Present Invention

The inventors of the present invention also created variants of the above mentioned polypeptides. For this purpose, mutations where introduced in the sequence of SEQ ID NO: SEQ ID NO:105.

TABLE 4

| Clone | Mut1 | Mut2 | Mut3 | Mut4 |
|---|---|---|---|---|
| 1 | K17E | H51Q | | |
| 2 | T127I | | | |
| 3 | K28N | T86A | G154C | |
| 4 | N126S | A16I | | |
| 5 | G85D | | G119S | |
| 6 | A16I | F36L | A46V | I80T |
| 7 | G166S | E172R | T173N | A174R |
| 8 | E172G | T173N | A174R | |
| 9 | V26A | Q114P | | |
| 10 | N138D | G154S | K171I | |

Table 5 below illustrates the results of these mutations on the activity for the fusion protein of SEQ ID NO:105. As used herein, strain DSM 346 refers to *Staphylococcus aureus* strain DSM 346 (Leibniz-Institut DSMZ—Deutsche Sammlung von Mikroorganismen and Zellkulturen GmbH, Braunschweig, Germany). S64 and S69 are *Staphylococcus aureus* strains S64 and S69 obtained from Prof. Rob Lavigne (Katholieke Universiteit Leuven, Belgium).

TABLE 5

| Clone | Strain | MIC [µg/mL] |
|---|---|---|
| 1 | DSM 346 | 4 |
|  | S64 | 6 |
|  | S69 | 6 |
| 2 | DSM 346 | 2 |
|  | S64 | 4 |
|  | S69 | 4 |
| 3 | DSM 346 | 4 |
|  | S64 | 8 |
|  | S69 | 8 |
| 4 | DSM 346 | 2 |
|  | S64 | 4 |
|  | S69 | 4 |
| 5 | DSM 346 | 4 |
|  | S64 | 4 |
|  | S69 | 4 |
| 6 | DSM 346 | 6 |
|  | S64 | 20 |
|  | S69 | 12 |
| 7 | DSM 346 | 6 |
|  | S64 | 10 |
|  | S69 | 8 |
| 8 | DSM 346 | 4 |
|  | S64 | 6 |
|  | S69 | 6 |
| 9 | DSM 346 | 4 |
|  | S64 | 4 |
|  | S69 | 4 |
| 10 | DSM 346 | 4 |
|  | S64 | 6 |
|  | S69 | 8 |

All mutants retained antibacterial activity on *S. aureus*.

Some of the above mentioned mutations were also verified for the sequence of SEQ ID NO: 107. In addition, some of the above mutations were combined. In addition, mutation G154S was used instead of G154C. Table 6 below illustrates the mutations tested for the fusion protein of SEQ ID NO: 107.

TABLE 6

| Clone | Mut1 | Mut2 | Mut3 | Mut4 | Mut 5 | Mut 6 |
|---|---|---|---|---|---|---|
| 11 | K17E | H51Q |  |  |  |  |
| 12 | K17E | H51Q | E172G | T173N | A174R |  |
| 13 | K28N | T86A | G154S |  |  |  |
| 14 | K28N | T86A | G154S | E172G | T173N | A174R |
| 15 | K17E | H51Q | K28N | T86A | G154S |  |

TABLE 6-continued

| Clone | Mut1 | Mut2 | Mut3 | Mut4 | Mut 5 | Mut 6 |
|---|---|---|---|---|---|---|

Table 7 below illustrates the results of these mutations on the activity for the fusion protein of SEQ ID NO: 107.

TABLE 7

| Clone | Strain | MIC [µg/mL] |
|---|---|---|
| 11 | DSM 346 | 4 |
|  | S64 | 4 |
|  | S69 | 12 |
| 12 | DSM 346 | 8 |
|  | S64 | 10 |
|  | S69 | 10 |
| 13 | DSM 346 | 4 |
|  | S64 | 4 |
|  | S69 | 4 |
| 14 | DSM 346 | 10 |
|  | S64 | 8 |
|  | S69 | 8 |
| 15 | DSM 346 | 2 |
|  | S64 | 4 |
|  | S69 | 4 |

All mutants retained antibacterial activity on *S. aureus*.

In addition, thermal stability was assessed for two of said mutants in comparison to the unmodified fusion protein. The thermal stability assay was carried out with the strain *Staphylococcus aureus* DSM 346. The proteins were diluted to a concentration of 0.3 mg/ml followed by an incubation for 20 minutes at different temperatures (see table 8 below). A standard MIC assay was carried out after this incubation time. The higher the temperature after which the protein still shows (a high) activity, the better is the thermal stability of a protein.

TABLE 8

| | MIC [µg/mL] | | | | | | |
|---|---|---|---|---|---|---|---|
| | RT | 44.6° C. | 47.1° C. | 49.7° C. | 52.3° C. | 54.9° C. | 57.4° C. | 60° C. |
| SEQ ID NO: 107 | 6 | 20 | 25 | 30 | 30 | >30 | >30 | >30 |
| Clone 11 | 4 | 6 | 10 | 10 | 16 | >30 | >30 | >30 |
| Clone 15 | 4 | 4 | 4 | 4 | 4 | 4 | 6 | 8 |

Clones 11 and 15 thus showed increased thermal stability in comparison to the unmodified fusion protein.

The invention claimed is:

1. A polypeptide comprising:
   i) the CHAP domain of LysK endolysin or a variant thereof;
   ii) the M23 endopeptidase domain of lysostaphin;
   iii) the cell wall binding domain (CBD) of ALE-1, and
   iv) a further peptide selected from the group consisting of an antimicrobial peptide, an amphipathic peptide, a cationic peptide, a hydrophobic peptide, a sushi peptide and a defensin
   wherein said variant sequence exhibits mutation H8N and/or T43A compared to the amino acid sequence of SEQ ID NO:1, and wherein the CHAP domain of LysK endolysin is SEQ ID NO: 1; the M23-endopeptidase domain is SEQ ID NO: 3, and the CBD is SEQ ID NO: 5.

2. The polypeptide according to claim 1, wherein the polypeptide comprises the amino acid sequence of SEQ ID NO:1, SEQ ID NO:3 and of SEQ ID NO:5.

3. The polypeptide according to claim 1, wherein the polypeptide comprises:
   i) the amino acid sequence of SEQ ID NO:2, or of a variant sequence thereof exhibiting one or more mutations selected from the group consisting of K16E, K27N, H50Q, T85A, G153S, G153C compared to the amino acid sequence of SEQ ID NO:2,
   ii) the amino acid sequence of SEQ ID NO:4, and/or
   iii) the amino acid sequence of SEQ ID NO:6.

4. The polypeptide according to claim 3, wherein said variant sequence exhibits at least mutations K16E and H50Q compared to the amino acid sequence of SEQ ID NO:2.

5. The polypeptide according to claim 1, wherein the polypeptide comprises one or more sequences selected from the group consisting of SEQ ID NO:2, SEQ ID NO:4 and SEQ ID NO:6.

6. The polypeptide according to claim 1, wherein the polypeptide comprises the amino acid sequence of SEQ ID NO:2, SEQ ID NO:4 and SEQ ID NO:6.

7. The polypeptide according to claim 1, wherein the order of elements or of their respective variants is from the N- to the C-terminus:
   a) CHAP domain—M23-endopeptidase domain—CBD of ALE-1—peptide, or
   b) Peptide—CHAP domain—M23-endopeptidase domain—CBD of ALE-1.

8. The polypeptide according to claim 1, wherein the further peptide is:
   i) an antimicrobial peptide selected from the group consisting of the SEQ ID Nos. from SEQ ID NO: 40 to 94,
   ii) an amphipathic peptide selected from the group consisting of SEQ ID NO: 98, SEQ ID NO: 99 and SEQ ID NO: 100,
   iii) a cationic peptide selected from the group consisting of the SEQ ID Nos. from SEQ ID NO: 11 to 39,
   iv) a sushi peptide according to SEQ ID NO: 95, or
   v) a hydrophobic peptide selected from the group consisting of SEQ ID NO: 96 and SEQ ID NO: 97.

9. The polypeptide according to claim 8, wherein the further peptide is selected from the group consisting of SEQ ID NO: 38 and SEQ ID NO: 94.

10. The polypeptide according to claim 1, wherein the polypeptide comprises a sequence selected from the group consisting of SEQ ID NO:105, SEQ ID NO: 107, SEQ ID NO:109 and SEQ ID NO:111.

11. The polypeptide according to claim 1, wherein said polypeptide is capable of degrading the cell wall of *Staphylococcus aureus* bacteria.

12. A polypeptide comprising a variant sequence of SEQ ID NO:1, wherein said variant sequence exhibits mutation H8N and/or T43A compared to the amino acid sequence of SEQ ID NO:1.

13. A polypeptide comprising a variant sequence of SEQ ID NO:2, wherein said variant sequence exhibits one or more mutations selected from the group consisting of K16E, K27N, H50Q, T85A, G153S, G153C compared to the amino acid sequence of SEQ ID NO:2.

14. The polypeptide according to claim 13, wherein said variant sequence exhibits at least mutations K16E and H50Q compared to the amino acid sequence of SEQ ID NO:2.

15. The polypeptide according to claim 13, wherein said variant sequence exhibits at least mutations K16E, K27N, H50Q, T85A, and G153S compared to the amino acid sequence of SEQ ID NO:2.

16. The polypeptide according to claim 13, wherein said polypeptide further comprises the sequence of at least one catalytic domain of a peptidoglycan hydrolase and/or exhibits antibacterial activity.

17. The polypeptide according to claim 16, wherein said polypeptide comprises the sequence of SEQ ID NO: 108 or SEQ ID NO: 110.

18. A nucleic acid encoding a polypeptide according to claim 1.

19. A vector comprising a nucleic acid according claim 18.

20. A host cell comprising a polypeptide according to claim 1.

21. A composition comprising a polypeptide according to claim 1, wherein the composition is an aqueous solution, a powder, a suppository, an emulsion, a suspension, a gel, a lotion, a cream, salve, ointment, injectable solution, syrup, spray, inhalant, a coating composition, a stent coating composition, or a catheter coating composition, or a biomaterial.

22. A device comprising a polypeptide according to claim 1, wherein the device is a medical device.

23. A method for the treatment of the human or animal body by surgery or therapy or in diagnostic methods practiced on the human or animal body comprising administering to a subject in need thereof a polypeptide according to claim 1.

24. The method according to claim 23, wherein the polypeptide treats or prevents bacterial infections in a subject.

25. The method according to claim 23, wherein the polypeptide treats a wound of a subject, or for the treatment of dermatitis or otitis.

26. A method for disinfecting an inanimate surface, composition and/or object, comprising contacting said surface, composition or object with a polypeptide according to claim 1.

27. A method for preventing contamination of an inanimate surface, composition and/or object with bacteria, comprising contacting said surface, composition or object with a polypeptide according to claim 1.

28. The polypeptide according to claim 13, wherein said polypeptide further comprises the sequence of at least one catalytic domain of a peptidoglycan hydrolase and/or exhibits antibacterial activity against *S. aureus*.

29. The composition comprising a polypeptide according to claim 21, wherein the biomaterial is a bone cement.

30. The composition comprising a polypeptide according to claim 21, wherein the aqueous solution is a buffer or a physiological solution.

31. The composition comprising a polypeptide according to claim 21, wherein the coating composition is an implant coating composition.

32. The method according to claim 24, wherein the polypeptide treats or prevents a bacterial infection in a subject.

33. The method according to claim 25, wherein the wound is an acute wound or chronic wound.

34. The method according to claim 25, wherein the acute wound is an iatrogenic wound.

35. A method for disinfecting a nosocomial environment or a doctor's office comprising contacting a surface, composition or object with a polypeptide according to claim 1.

36. The method according to claim 27, wherein the bacteria is *Staphylococcus aureus*.

37. The method according to claim 32, wherein the bacterial infection is by *Staphylococcus aureus* bacteria.

\* \* \* \* \*